United States Patent
Jessen et al.

(10) Patent No.: US 11,636,916 B1
(45) Date of Patent: Apr. 25, 2023

(54) BIOLOGICAL CELL SIMULATION HEURISTICS RANKING

(71) Applicant: X Development LLC, Mountain View, CA (US)

(72) Inventors: Johan Jessen, San Francisco, CA (US); Ivan Grubisic, Oakland, CA (US)

(73) Assignee: X Development LLC, Mountain View, CA (US)

( * ) Notice: Subject to any disclaimer, the term of this patent is extended or adjusted under 35 U.S.C. 154(b) by 1328 days.

(21) Appl. No.: 15/976,576

(22) Filed: May 10, 2018

(51) Int. Cl.
*G16B 5/00* (2019.01)
*G16B 40/00* (2019.01)
*G16B 45/00* (2019.01)

(52) U.S. Cl.
CPC ............... *G16B 5/00* (2019.02); *G16B 40/00* (2019.02); *G16B 45/00* (2019.02)

(58) Field of Classification Search
CPC .......... G16B 5/00; G16B 40/00; G16B 45/00
See application file for complete search history.

(56) References Cited

U.S. PATENT DOCUMENTS

| 2012/0066378 A1* | 3/2012 | Lui ..................... G06F 11/3636 709/224 |
| 2019/0139622 A1* | 5/2019 | Osthege ................. G16B 20/00 |

FOREIGN PATENT DOCUMENTS

| WO | WO 2014/015196 A2 | 1/2014 | |
| WO | WO-2017134602 A1 * | 8/2017 | ............. G16B 35/00 |

OTHER PUBLICATIONS

Karr, J.R., et al., A whole-cell computational model predicts phenotype from genotype. Cell, 150(2), pp. 389-401. (Year: 2012).*
Lee, R., Karr, J.R. and Covert, M.W. WholeCellViz: data visualization for whole-cell models. BMC bioinformatics, 14(1), pp. 1-9. (Year: 2013).*

* cited by examiner

*Primary Examiner* — Lori A. Clow
*Assistant Examiner* — Janna Nicole Schultzhaus
(74) *Attorney, Agent, or Firm* — Kilpatrick Townsend & Stockton LLP

(57) ABSTRACT

A whole cell model may be constructed and used to simulate cell behavior. The whole cell model may have a baseline cell state that can be perturbed by a user in order to understand the behavior and importance of various molecules, processes and/or sub-models within the whole cell model. The simulation data is evaluated according to a variety of heuristics. The simulation data is ranked within each heuristic. The heuristic evaluation of the simulation data is then compared to an input perturbation to determine the relative importance of the heuristics. The output is a visualization of the simulation data according to each heuristic within a dynamic ranked display.

18 Claims, 13 Drawing Sheets

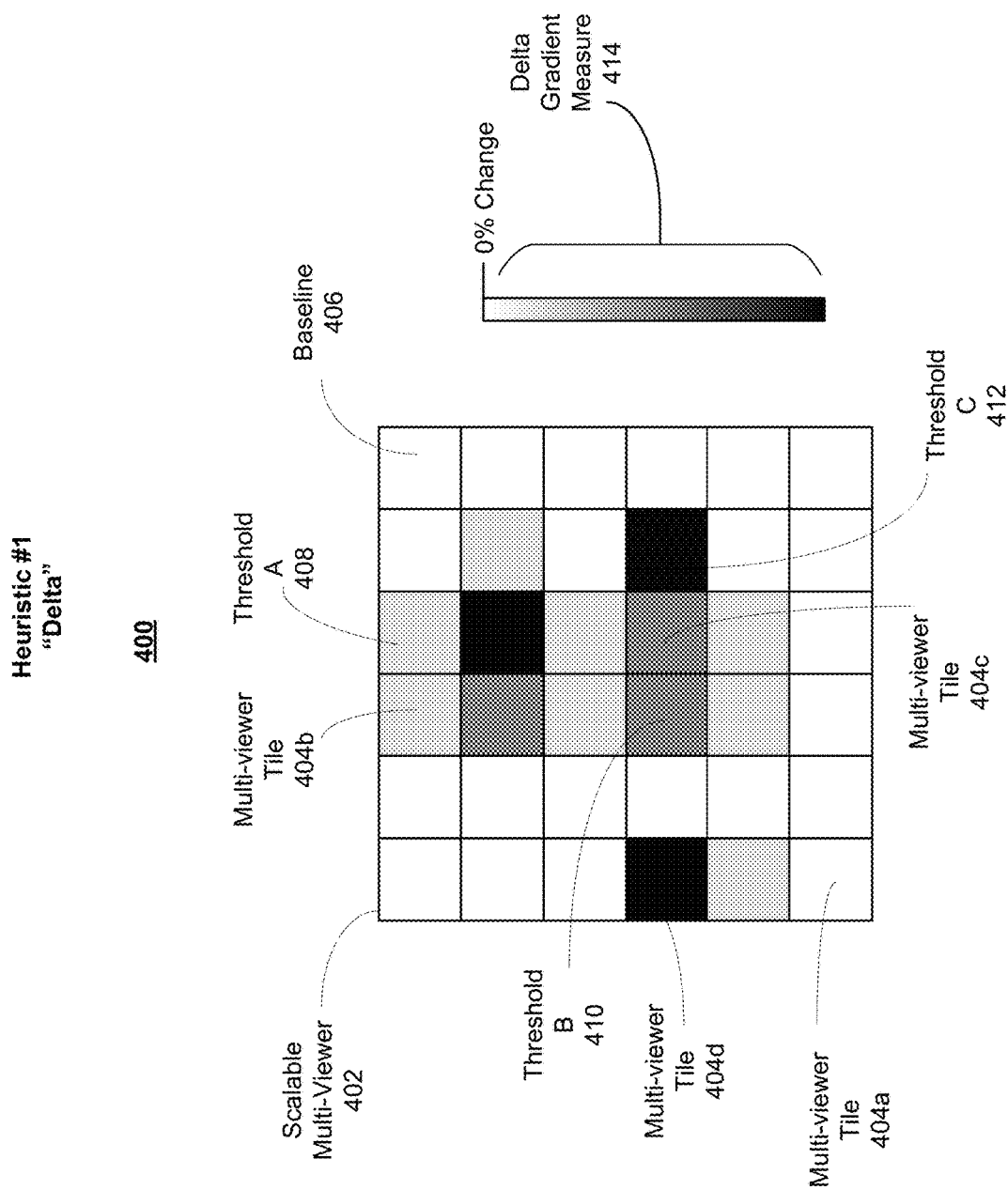

Heuristic #5
"Error"

BIOLOGICAL CELL SIMULATION HEURISTICS RANKING

BACKGROUND

Field of Art

This description generally relates to ranking heuristic measurements of the behavior of a model system of a cell, and specifically to ranking by relevance to an input perturbation of the model system.

Description of the Related Art

A model system of a whole cell may be made up of hundreds of molecules, any number of sub-units, connecting relationships and reactions, etc. and may be so complex that evaluating the significance or meaning of the output simulation data may be challenging. If all the simulation data is presented to a user, the result may be overwhelming, preventing a user from drawing conclusions from the model system. Still more challenging is presenting simulation data of significance to a user of the simulation system, for example that allows a user to understand the effects of the initial conditions on the resulting cell behavior. Likewise there is a challenge of presenting items of the simulations which might be correlative, such as related reactions, related reactants, related products, etc. Another challenge might arise when the user attempts to compare different simulations against one another as the amount of data grows multiplicatively.

SUMMARY

A biological cell's functions and structure can be conceptualized as a model system of linked sub-units that operate together to simulate behavior of a whole cell. The whole cell can thus be broken down into various linked macro-level functions, including the process of cell metabolism, the generation of physical elements like cell walls and membranes, the processes of transcription and translation, the generation of proteins and other macromolecules, etc.

In a dynamic model system, different initial conditions may lead to different output cell behaviors, such that by altering inputs to the model system, a researcher can produce different responses of the model and thus mimic in vivo experiments. For example, initial conditions may alter the presence or absence of reactants, the amount of reactants, availability of enzymes, introduce a gene mutation, gene knockout, change growth time scales, etc. The result of a simulation of the model system is output simulation data which describes the response of the whole cell to the input initial conditions. The output simulation data may comprise molecule concentrations, reaction rates, and so on.

A whole cell model may thus be constructed and used to simulate cell behavior. The whole cell model may have a baseline cell state that can be perturbed by a user in order to understand the behavior and importance of various molecules, processes and/or sub-models within the whole cell model. The simulation data is evaluated according to a variety of heuristics. The simulation data is ranked within each heuristic. The heuristic evaluation of the simulation data is then compared to an input perturbation to determine the relative importance of the heuristics. The output is a visualization of the simulation data according to each heuristic within a dynamic ranked display.

A method for ranking a set of outcomes of a simulation of a biological cell is described herein. The method accesses a set of outcomes of the simulation of the biological cell. Each outcome is associated with a time step of the simulation and an outcome type of a plurality of outcome types. The method ranks, within the outcome type and the time step, each of the set of outcomes to form a set of per-type outcome rankings. The method ranks, across at least two outcome types and two time steps, each of the set of outcomes to form a set of cross-type outcome rankings. The method provides for display to a user a ranked list from the set of per-type outcome rankings and the set of cross-type outcome rankings. Each ranking is based at least in part on a correlation between each outcome and a perturbation of the simulation of the biological cell.

BRIEF DESCRIPTION OF DRAWINGS

FIGS. 4A-4B are illustrations of a delta heuristic, according to one embodiment.

DETAILED DESCRIPTION OF DRAWINGS

Figure 1:
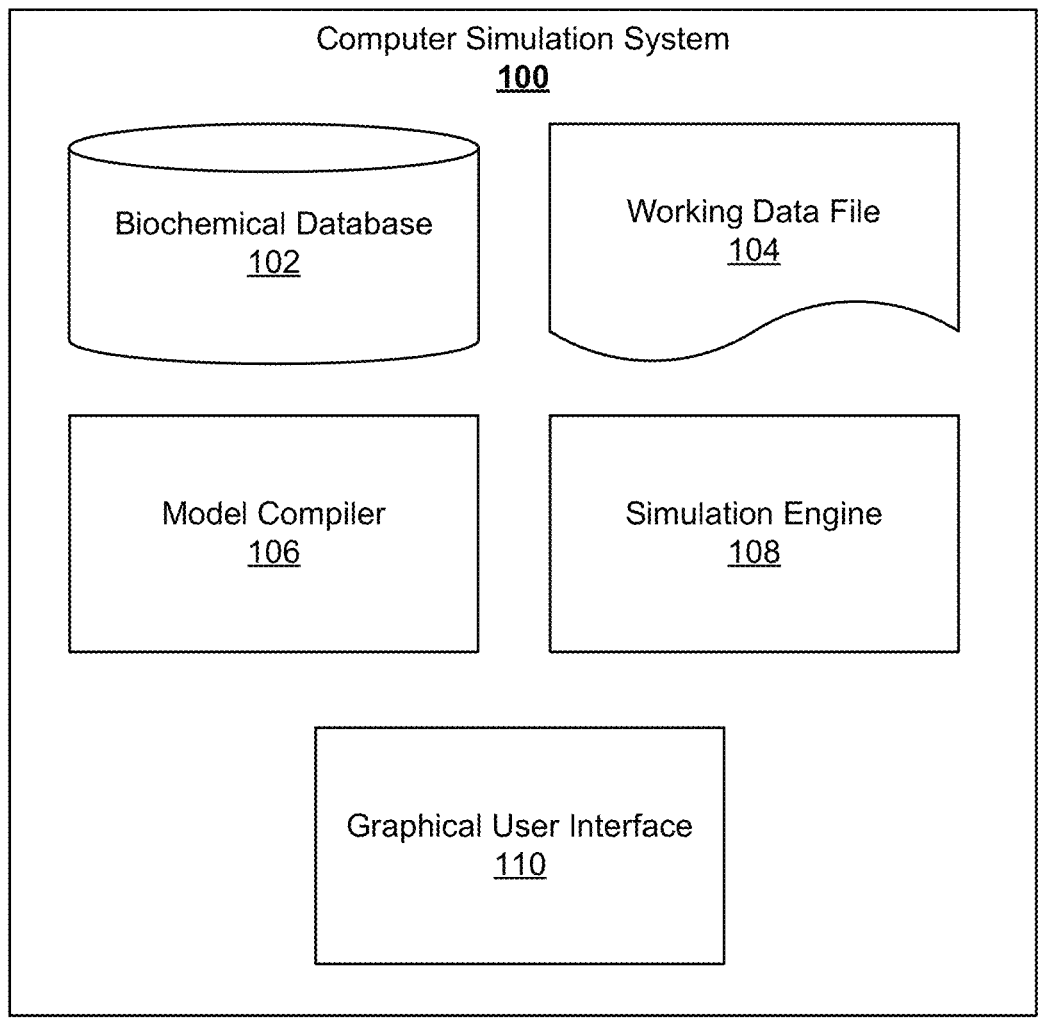
FIG. 1 is a block diagram illustrating computation components of a simulation system for modeling the behavior of a biological cell, structured in an exemplary embodiment as a bipartite graph.

A cell's functions and structures can be translated into a linked network of pathways between reactants and products that together form a model system of the cell. The linked network can be structured on several different levels. At a baseline level, the linked network is a reaction network of molecule nodes, process nodes and edges linking the molecule nodes to the processes in which they participate. At a second level, the linked network can be divided into interacting sub-units, which may represent different cellular processes, such as metabolism, transcription, translation, cell division, etc. To conduct research on the cell, simulations of the model system are run that may perturb normal cell functions. For example, if a researcher wants to know the effect of a specific reaction pathway on cell growth, the reaction pathway can be blocked from the simulation, and the resulting simulated cell growth rate determined.

The model system is a powerful way of researching a cell, since it allows a researcher to test a hypothesis without having to make choices about wet lab techniques and with significantly reduced time overheads. In some cases, the model system allows a researcher to isolate portions of a cell that may otherwise be impossible to study alone when working with live cells. However, the sheer size of the linked network and amount of information output from the model system may make it difficult for a researcher to identify what simulation results are important, and which changes to the model are most closely linked to a hypothesis they are testing.

To streamline a researcher's evaluation of the simulation data, a method of ranking simulation data is described herein. Simulation data is evaluated using a number of "heuristics" common to each simulation, which describe the outcomes of the simulation using different metrics and groupings. The heuristics are described in further detail with reference to FIGS. 4A-10. The results of the simulation are ranked within each heuristic to form a set of "per-type" outcome rankings. For example, if the heuristic measures changes in reaction rates of the cell (as described in FIGS. 4A-4B), then the simulation data may be evaluated by ranking the changes in reaction rates according to a percent change from an established baseline rate.

In addition, simulation data may be ranked between different heuristics to form a set of "cross-type" rankings. For example, a heuristic measuring changes in reaction rates might be compared to a "disruptive factor" heuristic, which measures the effect of a perturbation on the overall cell growth. While there might be a large increase in a reaction rate, it might not be as important as the perturbation leading to cell death, and thus the "disruptive" factor is ranked higher than the "delta" heuristic.

Using both the heuristic rankings and the cross-type rankings, a final output ranking is determined and graphically displayed to a researcher. Ultimately, the output of the simulation should show the researcher information that is most relevant to a hypothesis a researcher is testing with the model system. The final output ranking thus measures a distance to intent that compares the correlation between the simulation outcome types and a mathematical or parameter perturbation of the model system that was used to investigate a researcher's hypothesis. The translation between a perturbation of the model system and a researcher's input hypothesis may be determined through natural language processing. This ranking may be displayed in addition to the heuristic and cross-type rankings.

Lastly, the method may track a researcher's interactions with the simulation data to learn over time which heuristic is most useful. The tracking is used as a feedback to the per-type, cross-type, and final output rankings. For example, if a reaction rate change is frequently highly ranked, but a researcher is more interested in knowing how many submodels of the model system are affected by input perturbation, then the ranking down-ranks the reaction rate heuristic. Feedback may be determined per individual researcher, within a research team, or across multiple research teams. The method is described in further detail below.

I. Simulation Model of a Simulation

FIG. 1 is a block diagram illustrating computational components of a computer simulation system 100 (herein referred to as simply "simulation system") for modeling the behavior of a biological cell, in accordance with an embodiment. Depending on the embodiment, each component of the simulation system 100 may be implemented on one or more servers or other computational devices that are configured to communicate over a network (e.g. the Internet, a local area network, etc.). Alternatively, all computational components may be locally present on a single computational device. The computational components making up the simulation system 100 shown in FIG. 1 are a biochemical database 102, a working data file 104, a model compiler 106, a simulation engine 108, and a GUI 110. The GUI 110 may be the GUI 1200, and is described in further detail with reference to FIG. 12.

The biochemical database 102 is a database that stores data regarding molecules and processes that may be present or may occur in a biochemical environment simulated using the simulation system 100. The biochemical database 102 stores compositional data for each molecule that may be of use in the simulation, as well as data specifying how each molecule may be involved in one or more processes simulated by the simulation system 100. The biochemical database 102 may, more specifically, include information describing an organism at various levels of specificity. For example, on a more detailed level, the biochemical database 102 includes a catalog of an organism's genes, transcripts, proteins, etc. At a higher level of generality, the biochemical database 102 may include structures such as an organism's protein complexes. Although any database structure may be used to implement the biochemical database 102, in one embodiment the biochemical database 102 is implemented as a bipartite reaction network, which is described in further detail with reference to FIG. 2. Those of skill in the art will recognize that the same biochemical could be stored in another type of data structure.

The working data file 104 (sometimes referred to as the working file) is a set of instructions for configuring the simulation system 100. The simulation system 100 may be configured to simulate a single set of molecules and processes and, therefore, is not configured separately for each use of simulation system 100. Alternately, the working file 104 is used to select the molecules and processes to be simulated in the simulation system 100, and is therefore configured separately for each use of the simulation system 100. Additionally, the working file 104 may designate the specific cell functions to be modelled as well as the models to be included in the simulation system 100. Furthermore, the working file 104 may include parameters for one or more submodels included in the simulation system 100, as well as a set of initial conditions for each of those models.

The model compiler 106 uses working file 104 to compile the simulation system 100 so that simulations can be run. The model compiler 106 accesses the data retrieved from the biochemical database 102 and the working file 104 to generate various components of each simulation, examples of which include but are not limited to: a stoichiometric matrix, a bipartite network link molecule and process nodes, initial flux vectors that describe the rate of production and/or consumption of molecules, and quantities prior to a model being run for the first iteration, an objective function for each model, and any constraints on any of the models. After processing the various components of the simulation, the model compiler 106 outputs a simulation configuration data file (sometimes referred to as a configuration file or simconfig file). The configuration file is an input to the simulation engine 108 to generate a simulation of the cellular process described by the working file 104. In some implementations, the configuration file is a set of instructions to be executed by the simulation engine to accurately generate a simulation.

The simulation engine 108 manages the execution of the configuration or simconfig file produced by the model compiler 106 to simulate a biochemical process using the simulation system 100. The simulation engine 108 may initialize a given simulation using the initial conditions as constructed by the compiler 106 and as contained in the simconfig file. The simulation engine 108 creates an initial state vector, which includes the concentration of each molecule included in the simulation. The simulation engine 108 creates any initial exchange flux values into and out of each model in the simulation, which sets an initial rate of consumption and production for the associated molecules. The simulation engine 108 then iterates through a time step of the simulation, running the models of the simulation with the input state vectors and fluxes. Generally, this involves the simulation engine 108 arriving at a solution of the model for a first time step after the initial state, where the time step is of a predetermined length. The solution for each model for that time step may include, but is not limited to, the concentrations of the molecules output by each model, the fluxes of those molecules, and any changes to the overall biochemical environment (e.g. temperature changes, pH changes, etc.) caused by the processes being simulated by each model.

After the completion of the initial time step of the simulation, the simulation engine 108 updates the initial state vectors, flux vectors, and any other relevant state vectors with the output of the initial time step. As a specific example, the simulation engine 108 may use the fluxes determined during the running of the models multiplied by the length of the predetermined time step to determine the new concentrations of the molecules included in the models of the simulation. As another specific example, the simulation engine 108 may also calculate the exchange fluxes that connect each model with each other model in the simulation. The simulation system 100 then runs a second time step of the simulation similarly to the first time step using the updated state vectors and any other parameters of the simulation. The simulation engine 108 continues this process for a number of time steps or until reaching a termination state or receiving a termination input.

II. Biochemical Database

In some examples, the biochemical database 102 stores a reaction network structured as a bipartite graph. A reaction network characterizes a reaction pathway, the inputs, and the outputs of any steps occurring along the reaction pathway. The bipartite graph consists of two distinct sets of nodes, molecule and process, which are connected by edges. A bipartite graph, additionally, includes input molecule nodes representing the input molecules of the reaction. Each of the input molecule nodes is connected to at least one of the intermediary, process node or an output molecule node by one or more edges.

Within a bipartite graph structuring of a reaction network, input molecule nodes represent the first products of a reaction. Depending on the number of molecule and process nodes in the pathways of the reaction network, there may be any number of additional molecule nodes and edges in the reaction network showing the reaction pathways from input molecule nodes to output molecule nodes. In one specific use of such a network, the output molecule nodes represent the outputs of a particular cell function (or set of cell functions) such as metabolism, and are the output boundary of the bipartite metabolic network.

A molecule node may represent small molecules such as water, carbon dioxide, protons, etc. or macromolecules such as proteins, lipids, alcohols, organic acids, vitamins, etc. A molecule node may also represent organism specific molecules such as transcripts, proteins, and protein complexes. A molecule node may contain a plurality of metadata fields to describe the molecule including the molecule name, a molecule formula, an amino acid sequence, a macromolecular structure, electrical charge, chemical or physical properties (pKa, melting point, solubility, etc.) and any component molecules. Additionally, some non-physical properties may be included in the metadata of a molecule node including drug interaction, 3D structure etc. A molecule node need not contain information for each one of the previously described metadata categories. In some examples, molecule nodes may have associated flux values. Flux values of molecule nodes represent a net rate of downstream consumption of the molecule and upstream production of a molecule. Flux values thus describe the "flow" of the molecule through a reaction network.

Process nodes describe molecular actions in a biochemical environment including but not limited to chemical reactions, regulatory interactions, binding, transport, or others. A process node includes a number of descriptive metadata fields that provide information about the process including but not limited to a list of molecules and their associated roles in the process, reaction rate information, and energy requirements for the process, sub-processes that may be involved in the process, or other more detailed information.

In alternate embodiments, the biochemical database 102 may store information describing cellular processes using a different representation from the bipartite representation example above. For example, a transcription sub-model modeling cell transcription may use transcripts and relative concentrations to construct a monomial distribution sampled at various time steps or sequence composition techniques to translate the sampled set of transcripts into an analysis of nucleoside triphosphate demand, for which a bipartite reaction network would be less useful than other representations.

III. Sub-Models in Cell Modeling

Figure 2:
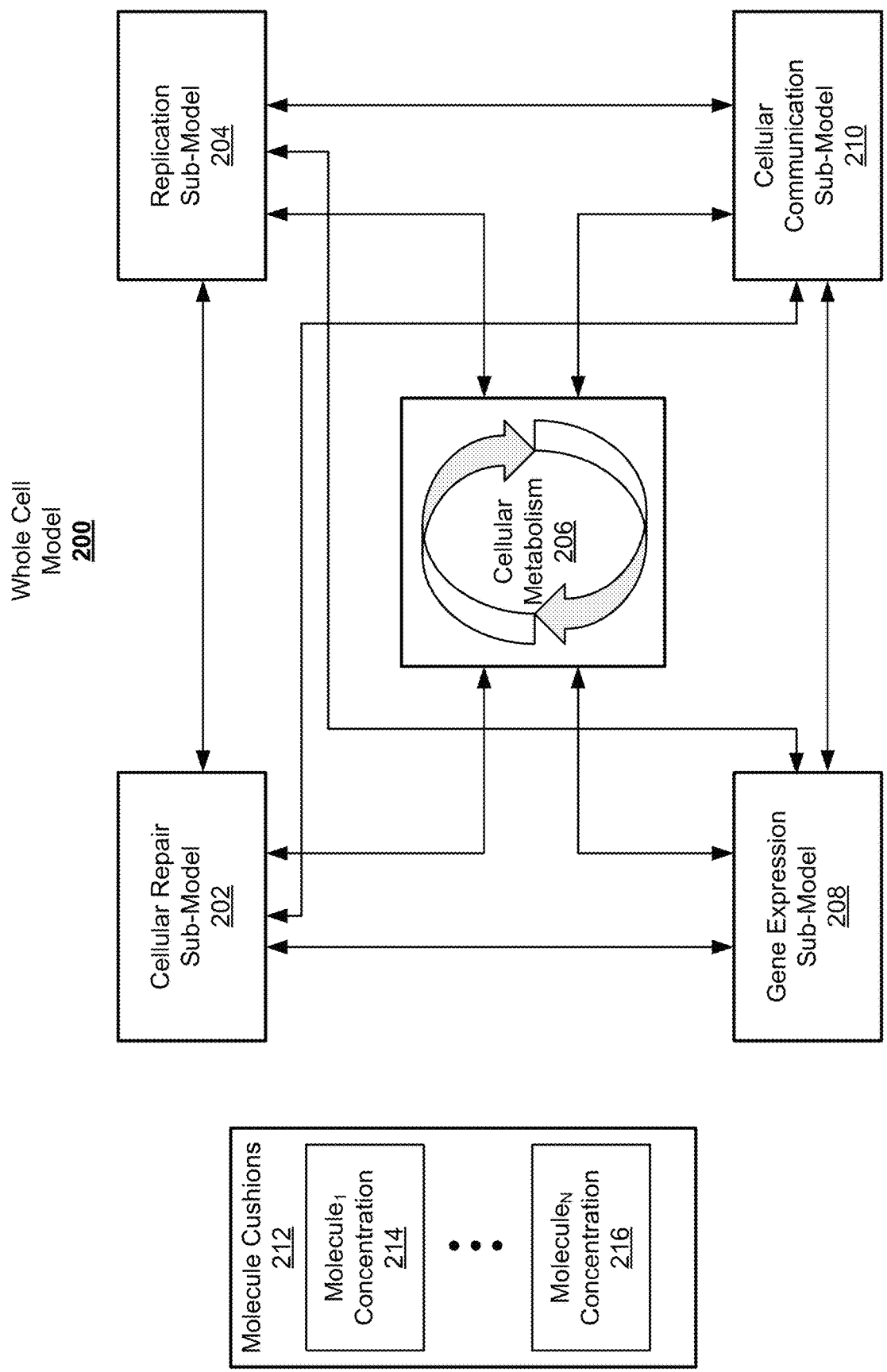
FIG. 2 is a block diagram of a full cell model, according to one embodiment.

FIG. 2 is a block diagram of a whole cell model 200, according to one embodiment. The whole cell model 200 contains a cellular metabolism 206 with any number of sub-models which input and/or output with other sub-models or the cellular metabolism 206. The sub-models include the cellular repair sub-model 202, the replication sub-model 204, the gene expression sub-model 208, and/or the cellular communication sub-model 210. The arrows leading to the cellular metabolism 206 represent the input flux and/or output flux values between the cellular metabolism 206. Arrows between sub-models and cellular metabolism 206 may also represent the supply of molecules from these sub-models to cellular metabolism 206.

As shown in FIG. 2, arrows lead from sub-models into cellular metabolism 206 and from cellular metabolism 206 into sub-models. This is an illustration of the fact that many cellular processes contain molecules and reaction pathways that are both inputs into cellular metabolism 206 and which are produced by cellular metabolism 206. Thus the sub-models shown in FIG. 2 may be both upstream sub-models and downstream sub-models, as described with reference to FIG. 1. The interactions between sub-models and cellular metabolism 206 may be coordinated by a single dataset that aggregates changes within the full cell model 200, such that each of the sub-models and cellular metabolism 206 receive and transmit information to the single dataset, rather than to each other.

In addition to molecule concentrations within sub-models and cellular metabolism 206, the full cell model 200 may include molecule cushions 212 that exist outside of system of supply and demand between the sub-models and cellular metabolism 206. The molecule cushions 212 represent reserves of molecules within the cellular environment. For example, molecule cushions 212 may be molecules that exist within a cell's cytoplasm, and which are available to molecular processes when needed. Molecule cushions 212 contain different reserve concentrations of different molecules. For example, a first molecule, $molecule_1$, may have a concentration of $molecule_1$ concentration 214. If $molecule_1$ is a molecule that has a large flux value or demand within the system of sub-models and cellular metabolism 206, then the reserve concentration of $molecule_1$ may be larger than other molecules with smaller demand. Thus the concentration of molecules within molecule cushions 212 may be proportional to the flux value associated with the molecule in cellular metabolism, the aggregate demand for the molecule within the sub-models, and/or any other measurement of demand within the system of sub-models and cellular metabolism 206. The molecule cushions 212 ensure that sudden increases in demand for a molecule within the full cell model 200 do not result in complete depletions of a molecule within the full cell model 200.

There may be any number of molecules within molecule cushions 212. A total of N molecules, represented by $molecule_N$ concentration 216, are assigned reserve concentrations within molecule cushions 212. In some examples, all molecules within the full cell model 200 are assigned reserve concentrations within molecule cushions 212. In other examples, molecules with demand and/or flux values above a threshold are assigned reserve concentrations within molecule cushions 212, such that a subset of the molecules within the full cell model 200 representing the primary flow of molecules are stored in molecule concentrations $molecule_1$ concentration 214 through $molecule_N$ concentration 216.

The effect of the molecule cushions 212 on the full cell model 200 is that the molecule cushion concentrations allow the demand for a molecule to instantaneously (e.g., for a given single time step evaluating the subunits) exceed supply without disrupting the full cell model 200. This allows the production network to continue to function as a demand load is applied to the system of the full cell model 200, giving the cell time to increase production of the molecule to meet the new demand.

IV. Simulations of the Whole Cell Model

A simulation of the whole cell model 200 is a mathematical calculation across all sub-units of the whole cell model 200 and associated with the same set of initial input parameters. A single simulation produces a set of simulation data, which include all of the mathematical solutions to the equations describing the sub-units of the whole cell model 200. A simulation may iteratively solve the whole cell model 200 to produce simulation data over a time series, such that each time step is associated with a set of solutions to the whole cell model 200. Solutions for a single time step may be the result of a single, deterministic calculation, or a statistical mean from multiple iterations of solutions of one or more of the sub-units with the same initial conditions and at the same time step. This may be dependent on the type of equations describing each of the sub-units. For example, solutions may be determined from a single flux-balance-analysis (FBA) analysis of a metabolic sub-unit, or from 100 solutions of a sub-unit modeled with a Monte-Carlo method. The simulation data is evaluated using a number of heuristics, which are described in further detail with reference to FIGS. 3-11.

To produce simulations of the whole cell model 200 across a time scale, the solutions at a first time are used as the initial conditions for a subsequent time step. Time steps in the time series may be adjusted to prevent depletion of molecule concentrations, such that at high flow rates of molecules in the whole cell model 200, the time steps are smaller than when the rates of consumption and production are reduced. A collection of simulation data from multiple simulations of a whole cell model 200 comprise an "experiment."

V. Baseline and Perturbed Cell States

The whole cell model 200 has a set of initial conditions and cell parameters that lead to homeostasis of the whole cell model 200, which is referred to herein as a "baseline state." These initial conditions may include pH levels, molecule concentrations, molecule concentrations in extracellular fluid, and any other variables that lead to stable maintenance and internal regulation of the cell, as well as regular cell growth. In some examples, a baseline state for the whole cell model 200 is determined through a simulation of the whole cell model 200. In some examples, a baseline state is determined from primary source literature. A perturbation of the whole cell model 200 refers to any alteration of any of a cell's input variables that deviate from the baseline state. As described herein, a "perturbed cell" is a cell whose initial conditions deviate from the baseline cell. For example, a perturbation may be a change in molecule concentrations, a change in pH levels, a change in gene expression, an alteration in the extracellular environment, or any other input variable. In some examples, a perturbation is any of: blocking a reaction pathway in the simulation, removing a molecule from the simulation, removing a nucleic acid from the simulation, removing a growth factor from the simulation, adding a reaction pathway in the simulation, adding a molecule to the simulation, adding a nucleic acid to the simulation, and/or adding a growth factor to the simulation. A perturbation of the whole cell model 200 may lead to at least one interval between two time steps in a simulation in which the whole cell model 200 changes at least one value. In some examples, a perturbation of the whole cell model 200 leads to a change in the equilibrium state of the whole cell model 200. For example, a cell growth rate of a cell may be different before and after a perturbation of the whole cell model 200.

VI. Ranking Overview

Figure 3:
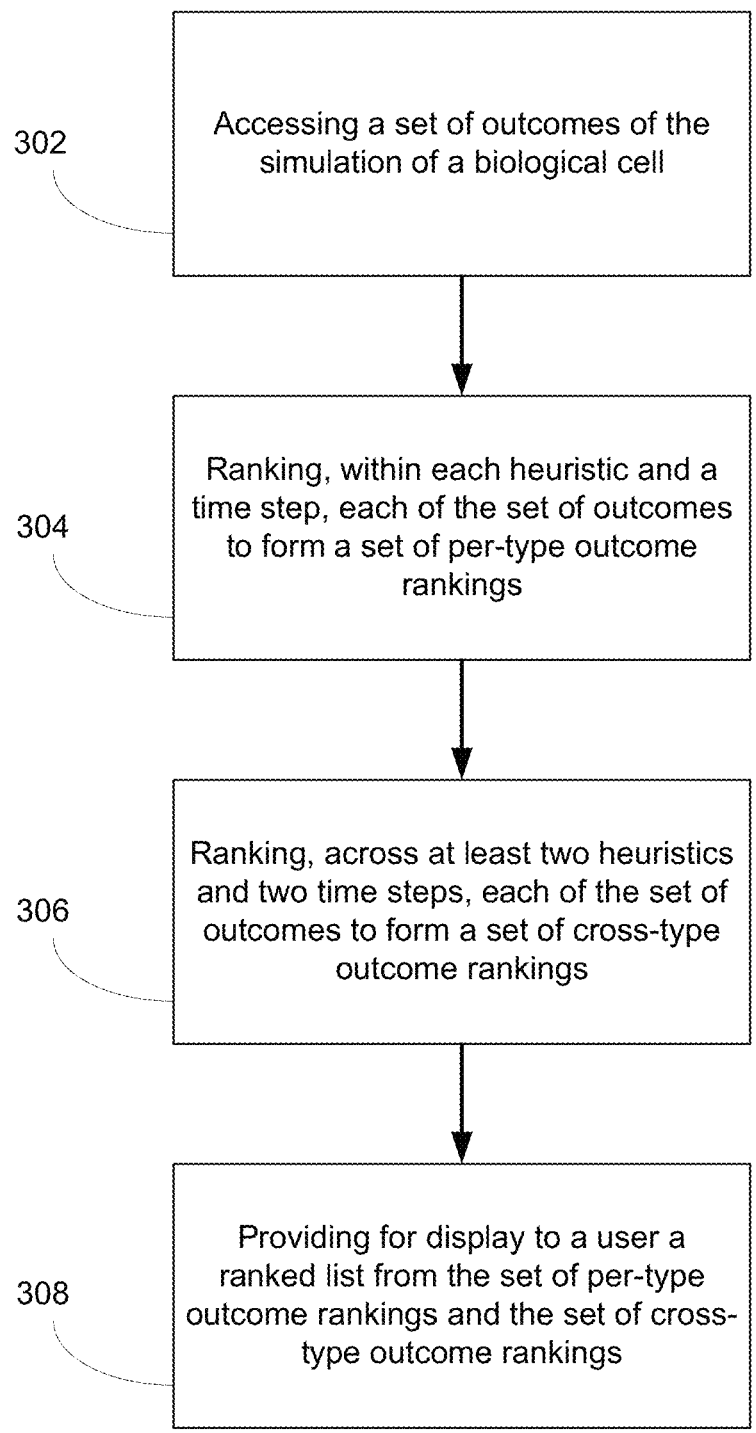
FIG. 3 shows a process for ranking a set of outcomes of a simulation of a biological cell, according to one embodiment.

FIG. 3 shows a process 300 for ranking a set of outcomes of a simulation of a biological cell, according to one embodiment. The process 300 ranks simulation data produced from solving the whole cell model 200 within heuristics to produce a set of per-type rankings. The process 300 ranks simulation data between heuristics to produce cross-type ranking. The process 300 allows a user to understand the impact of a perturbation on the whole cell model 200.

The process 300 may be implemented on one or more servers, processors, or other computational devices. In some examples, the one or more servers, processors, or other computational devices may be configured to communicate over a network (e.g. the Internet, a local area network, etc.). Alternatively, the process 300 may be implemented locally on a single computational device. In some examples, the process 300 may be implemented on a computational device in communication with a biochemical database, a model configuration file, a model compiler, and a simulation engine (not shown).

The process 300 begins by accessing 302 a set of outcomes of the simulation of the biological cell. The outcomes of the simulation of the biological cell are the data that results from solving the equations associated with the whole cell model 200. Each outcome is associated with a time step of a time series simulation of the whole cell model 200. When accessing the outcomes of the simulation data, the process 300 may access sets of outcomes from more than one time step. For example, the process 300 may access the outcomes from an initial time t=0 and the outcomes from a subsequent time t=1. Types of outcomes are described in further detail with reference to FIG. 4A-10. The outcomes of the simulation of the biological cell may be the raw output data from solving the equations associated with the whole cell model 200, and may not be processed or otherwise converted into form intelligible to a user.

The process 300 then ranks 304, within each heuristic and within each time step, each of the set of outcomes to form a set of per-type outcome rankings. The heuristics are groupings of the set of outcomes, calculations using the set of outcomes, and any other data processing of the set of outcomes. The heuristics are described in FIGS. 4A-10. Each of the heuristics provides a way of evaluating the set of outcomes, which allows a user to understand the effect of a perturbation on the whole cell model 200. Each of the heuristics may be visually communicated to a user using a single visualization, such that each heuristic can be easily identified by a user over multiple uses of the process 300, simulations or experiments of the whole cell model 200. The set of outcomes is ranked by heuristic and by a single time step to provide a snapshot view of the whole cell model's 200 behavior. Ranking within each heuristic and within each time step is described in further detail with reference to FIGS. 11-12.

The process 300 ranks 306, across at least two heuristics and two time steps, each of the set of outcomes to form a set of cross-type outcome rankings. Ranking across at least two heuristics and two time steps includes comparing the relative importance of one heuristic to another with respect to the perturbation on the whole cell model 200. For example, a heuristic evaluating changes in reaction rates may be more or less important than a heuristic evaluating overall cell growth. Comparing two time steps also allows for insight into the whole cell model's 200 behavior over a time series of the simulation. Using comparison across two time steps potentially provides a more meaningful context for the rankings of 304, since it is possible that changes within a single time step do not ultimately affect the cell's subsequent states or a final equilibrium state. By comparing across time steps, temporary changes in the behavior of the whole cell model 200 can be distinguished from long-term effects of an input perturbation. Ranking across at least two heuristics and two time steps is described in further detail with reference to FIGS. 11-12.

Lastly, process 300 provides 308 for display to a user a ranked list from the set of per-type outcome rankings and the set of cross-type outcome rankings. The display may be within a user interface (UI), or GUI, such as the GUI described in further detail with reference to FIG. 12. The display includes the visualizations associated with each of the heuristics. The visualizations may be presented in a ranked list, such that the outcomes of a simulation of the whole cell model 200 are ultimately displayed to a user through ranked heuristics, each of which has its own visualization. The ranking from the set of per-type outcome rankings and the set of cross-type outcome rankings is described in further detail with reference to FIGS. 11-12.

VII. Heuristics

A. Delta

Figure 4B:
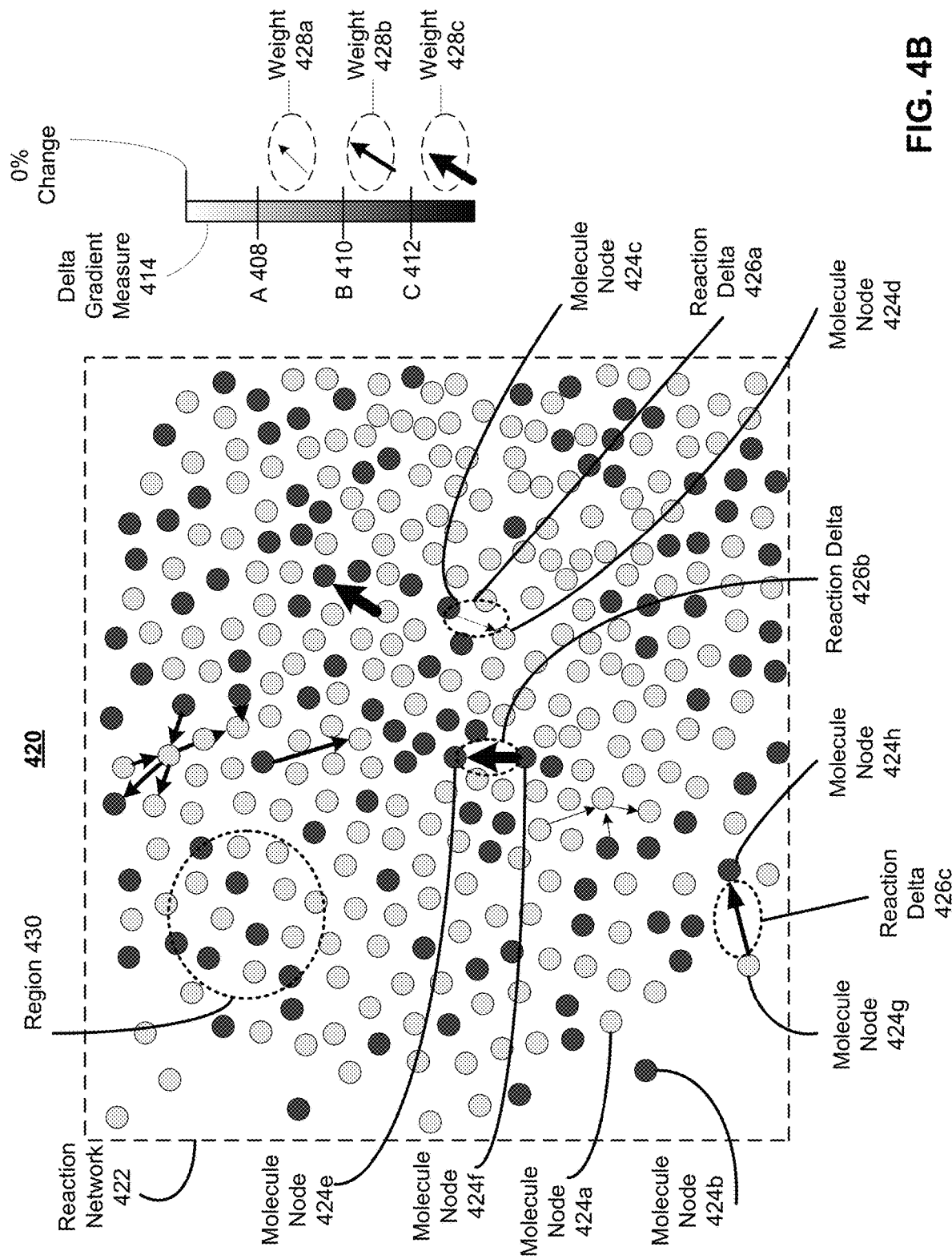

FIGS. 4A-4B are illustrations 400 and 420 of a delta heuristic, according to one embodiment. Illustration 400 may be a high level view from which the view in illustration 420 can be accessed in response to a user input, which is described in more detail below.

The delta heuristic is a differential evaluation between a baseline cell state and the simulation data output by at least one simulation of the whole cell model 200. The delta heuristic may determine a change in reaction rates between a baseline cell and a perturbed cell. Additionally or alternatively, the delta heuristic determines a change in the total number of reactions that occur. In some examples, the delta heuristic may compare between different time steps within a single simulation, such that the baseline cell is a cell state of a previous time step. In this example, the differential calculation is between the outcomes of the previous time step and the outcomes of a subsequent time step. To generate the delta heuristic, the raw simulation data is evaluated by determining an absolute difference between simulation data and baseline data. In some examples, the difference may be a numerical difference. Another calculation determines a ratio of simulation data to the baseline data to calculate a percent difference. In an example of the former calculation, data differentials can be calculate by taking the difference between reaction rates from the simulation data and the baseline data for a given reaction. In some examples, the delta heuristic may be determined by comparing average values between two time intervals. For example, the delta heuristic may determine a difference between reaction rates in the time interval t=0 and t=20 and the time interval t=20 and t=40. Any other differential or comparative calculation may be used to determine the delta heuristic.

The delta heuristic is conveyed to a user through a delta visualization, which allows a user to interpret the results of calculations associated with the delta heuristic in the context of the whole cell model 200. For example, physically locating the results of the delta heuristic within a map of the whole cell model 200 may allow a user to identify areas of interest within the whole cell model. A common visualization is used for each presentation of the delta heuristic to a user, which may be through a UI as described in further detail with referenced to FIGS. 11-12. A first example of a delta heuristic visualization is shown in FIG. 4A. A second example of a delta heuristic visualization is shown in FIG. 4B. It is to be understood that the delta heuristic visualization is not limited to either of these illustrations.

FIG. 4A shows an illustration 400 of the scalable multi-viewer 402 displaying a delta heuristic of simulation data. Any of the delta heuristic calculations described above may be used to produce the illustration 400.

A1. Scalable Multi-Viewer Delta Heuristic

The simulation map is divided up into multi-viewer tiles, such as the multi-viewer tiles 404a, 404b, 404c, and 404d (collectively 404). In this example, multi-viewer tiles are arranged into six rows and six columns, however the number of nodes, rows, and columns may vary by simulation and based on other factors as detailed below. Each of the multi-viewer tiles within the scalable multi-viewer correspond to portions of a reaction network, such that a subset of all of the reaction nodes and/or molecule nodes of the reaction network are represented by each multi-viewer tile. In some examples, a single multi-viewer tile corresponds to a single reaction node. In other examples, a single multi-viewer tile corresponds to a cluster of reaction nodes. In some examples, the scalable multi-viewer 402 may be shown simultaneously with the reaction network 422, such that reaction and/or molecule nodes shown in the visible tiles of the scalable multi-viewer 402 correspond to the reaction nodes displayed by the reaction network 422 as described in further detail with reference to FIG. 4B. The remaining of the multi-viewer tiles correspond to reaction nodes that are not simultaneously displayed as part of the reaction network 422, but are in the vicinity of those that are displayed.

In this context, vicinity refers to the relative number of reactions between the reaction nodes displayed as part of the reaction network 422 and other reactions (and their corresponding reaction nodes) that are part of a network of cell reactions, either being modeled by a particular model of the simulation or being modeled by any of the models of the simulations. The smaller the number of reactions between a given reaction and a reaction represented by one of the displayed nodes, the closer the vicinity and thus the more likely it is that such a reaction is represented by one of the multi-viewer tiles other than those associated with one of the reaction nodes displayed by the reaction network 422.

The scalable multi-viewer 402 accesses the delta heuristic data, and populates the scalable multi-viewer with a visualization of the delta heuristic data. For example, a delta gradient measure 414 may be used to translate a percent difference in reaction rates (or any other delta metric) to a grayscale between white (corresponding to 0% change in reaction rates from a baseline cell) to black (corresponding to 100% change in reaction rates from a baseline cell). In some examples, the delta gradient measure 414 may be broken up into different thresholds, such that instead of assigning gradient values, different grayscale values are assigned for ranges of change in reaction rates. For example, in a three threshold and four range system, changes in reaction rates between 0% and 25% may be white, 25% to 50% may be 25% black, 50% to 75% may be 50% black, and 75% to 100% may be 100% black. Thus the scalable multi-viewer 402 visually distinguishes its displayed multi-viewer tiles 404 depending on which thresholds the corresponding reaction node deltas exceeded during the simulation.

The illustration 400 shows an example of the incremental thresholds for a quantity differential versus baseline where there are three total thresholds and four corresponding ranges—threshold A 408, threshold B 410, and threshold C 412. In this example, threshold A 408 is smaller than threshold B 410 which is smaller than threshold C 412. Accordingly, the white tiles, such as multi-viewer tile 404a, correspond to a region of the reaction network with a percent change below threshold A 408. In some instances, the region with the percent change below threshold A 408 indicates a baseline state 406. The lightly shaded tiles, such as multi-viewer tile 404b, correspond to a region of the reaction network with a percent change between threshold A 408 and threshold B 410. The medium shaded tiles, such as multi-viewer tile 404c, correspond to regions of the reaction network with a percent change between threshold B 410 and threshold C 412. The black tiles, such as multi-viewer tile 404d, correspond to regions of the reaction network with a percent change between threshold C 412 and 100%.

Presented by the scalable multi-viewer 402, a user can easily distinguish regions of the reaction network which resulted in little to no effect or change for a given molecule or reaction as the result of an input perturbation. The scalable multi-viewer 402 thus provides a visualization of the delta heuristic that allows a user to easily distinguish between more or less important regions of the reaction network based on the delta heuristic evaluation of output simulation data. Likewise, a user can distinguish varying degrees of effect for a given molecule or reaction, thereby drawing their attention to aspects of the reaction network that were more heavily affected by a perturbation, and visually deemphasize portions of the reaction network that are unchanged.

A2. Reaction Network Delta Heuristic

FIG. 4B is an illustration 420 of the reaction network 422 displaying a delta heuristic of simulation data. Any of the delta heuristic calculations described above may be used to produce the illustration 420. The reaction network 422 shows the delta heuristic within the context of the reaction network 422, which may be a portion of a full reaction network.

The illustration 420 shows a portion of a full reaction network with molecule nodes 424a, 424b, . . . , and 424h and process nodes represented as arrows between molecule nodes. The magnitude of the delta heuristic is visually conveyed to a user through the line weight of the arrows between molecule nodes. For example, the line weight of the arrows between the molecule nodes may correspond to the percent change in reaction rates of the reactions represented by the arrows. Similarly to the illustration 100, the delta gradient measure 414 may be broken up into ranges by thresholds A 408, B 410 and C 412, where different line weights correspond to different ranges within the delta gradient measure 414. For example, a reaction rate change below threshold A 408 may not display a line between molecule nodes. Thus the lack of arrows between molecule nodes in region 430 visually indicate that any changes in reaction rates of processes connecting these nodes are below threshold A 408. A reaction rate change between threshold A 408 and threshold B 410 may be displayed with weight 428a. The reaction rate change between molecule node 424c and molecule node 424d is visually indicated by the reaction delta 426a show with weight 428a. A reaction rate change between threshold B 410 and threshold C 412 may be displayed with weight 428b. The reaction rate change between molecule node 424g and molecule node 424h is indicated by the reaction delta 426c shown with weight 428b. A reaction rate change between threshold C 412 and 100% may be displayed with weight 428c. The reaction rate change between molecule node 424f and 424e is indicated by the reaction delta 426b shown with weight 428c.

Additionally or alternatively, the delta heuristic may be displayed within the reaction network 422 by the color or grayscale applied to the molecule nodes. For example, the molecule nodes themselves may be assigned gradient values within the delta gradient measure 414. As shown in illustration 420, the range of percent change may be dividing into two intervals with a single threshold, such that the lightly shaded nodes indicate a delta heuristic below the threshold, and darkly shaded nodes indicate a delta heuristic above the threshold. For example, a threshold may be a 20% delta, and molecule node 424g is lightly shaded to indicate that the change associated with molecule node 424g is below 20%, whereas molecule node 424*h* is darkly shaded to indicate that the change associated with molecule node 424*h* is above 20%. In other examples, there may be any number of thresholds within the delta gradient measure 414, such that the molecule nodes within the reaction network 422 are assigned any number of different gradient values or shadings.

In some examples, the delta heuristic visually indicated by the weights 428*a*, 428*b* and 428*c* (collectively 428) may be generated from a change in a different set of values than the shading of molecule nodes within the reaction network 422. For example, the weights 428 may be generated from a delta heuristic evaluation of changes in reaction rates, whereas the molecule node shadings may be generated from a delta heuristic evaluation of changes in molecule concentrations. For example, the molecule node 424*g* may not have a change in concentration different from a baseline, but the reaction between molecule node 424*g* and molecule node 424*h*, shown as reaction delta 426*c*, may have a change in its reaction rate between threshold B 410 and C 412, which is then visually indicated to a user by the weight 428*b*.

After viewing the high level illustration 400 of the full reaction network broken down into multi-viewer tiles 404, a user may wish to view the delta heuristic in a more detailed visualization that includes molecule nodes and process nodes. The illustration 400 may display some of the same information as the reaction network 422. A user may be able to switch between illustration 400 and the reaction network 422 by providing a zoom input to a GUI. For example, the reaction network 422 may correspond to a single multi-viewer tile 404 within the scalable multi-viewer 402. The GUI 400 may receive a zoom input to zoom in on a multi-viewer tile 404 within the scalable multi-viewer 402. The GUI 400 may then display the reaction network 422 of illustration 420, allowing the user to view the molecules and reactions of interest (for example, as illustrated in FIG. 4F) to gain more insight into the underlying biological processes. Through user selection of individual reactions and compounds, the GUI 400 can provide linking information via icons or similar to other reaction nodes that interact with selected reactions and/or molecules, providing the user insight into how possible changes to selected molecules or reactions (e.g., through the introduction of a drug) would affect other parts of the reaction network 200. This is described in further detail with reference to FIG. 12.

B. Correlation

Figure 5:
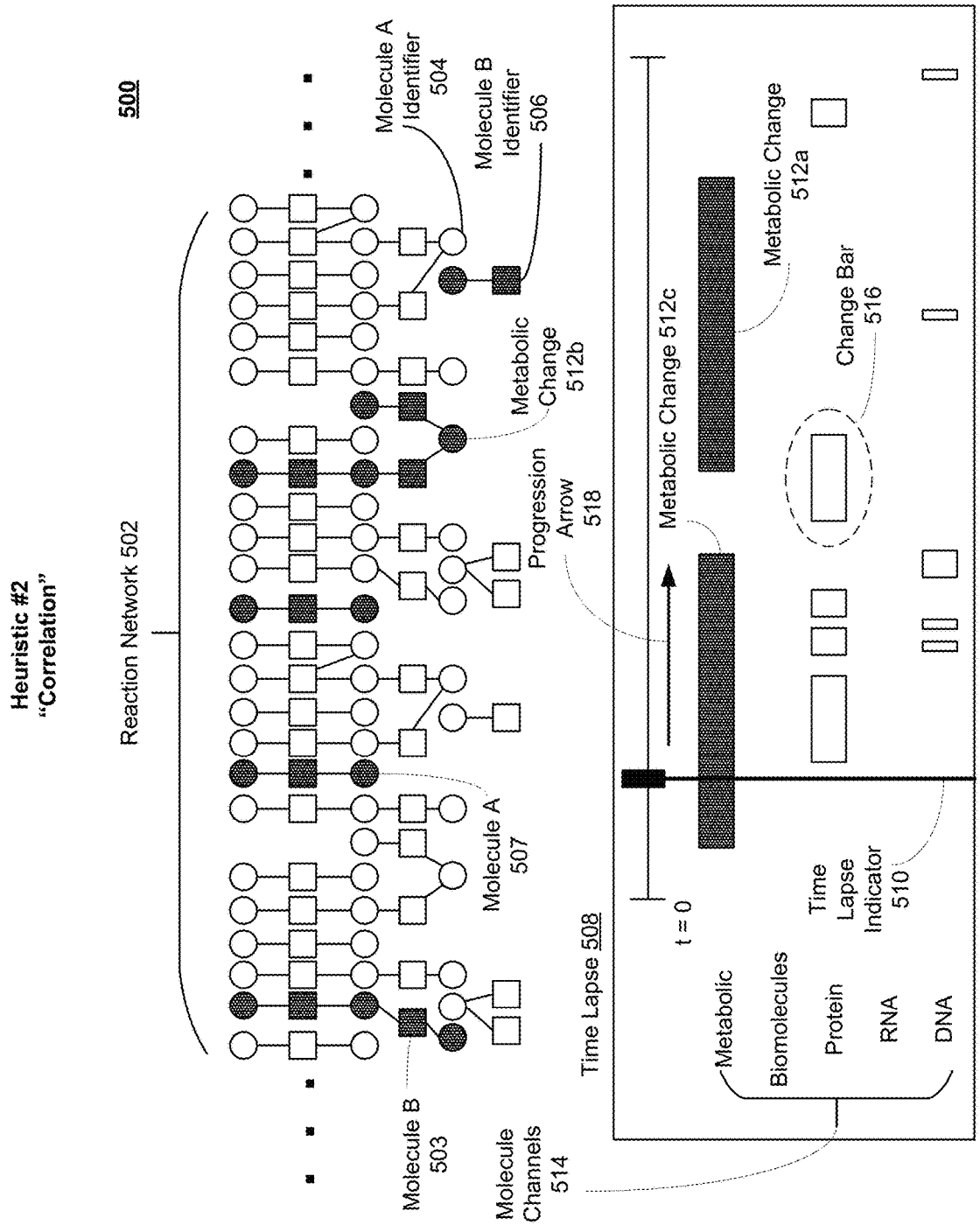
FIG. 5 is an illustration of a correlation heuristic, according to one embodiment.

FIG. 5 is an illustration 500 of a correlation heuristic, according to one embodiment. The correlation heuristic may be conveyed to a user in the illustration 500 by both a reaction network 502 and a corresponding time lapse 508, or separately as a reaction network 502 only or a time lapse 508 only.

A correlation heuristic evaluates whether a change in one element in a reaction network corresponds to changes in other portions of the reaction network. The correlation heuristic thus compares changes in the reaction network at a single time step to determine if they are coincident, i.e. occur at the same time within the same simulation. The correlation heuristic may compare changes in any variable of the simulation, such as a reaction rate, a molecule concentration, a pH level, etc. The correlation heuristic allows a user to understand how one change in one portion of the reaction network may relate to other changes in other portions of the reaction network. In some examples, the correlation heuristic provides a visualization that situates a change within a physical location in a representation of a reaction network. Additionally or alternatively, the correlation heuristic provides a visualization that situates a change within a time stamp in a time series of a simulation of the reaction network. These examples are described below.

B1. Reaction Network Correlation Heuristic

The reaction network 502 shows a portion of a full reaction network. Each of the molecule nodes within the reaction network 502 may be visually displayed by different molecule identifiers. For example, a molecule A identifier 504 is shown as a circle, whereas a molecule B identifier 506 is shown as a square. Molecule identifiers may mark the same molecule within the reaction network. For example, each of the molecules that are the same molecule as molecule A may be displayed within the reaction network 502 as circles. In some examples, the molecule identifiers may mark molecules within a molecule category, such as proteins, lipids, nucleic acids, or any other standard grouping or classification of molecules.

The changes that the correlation heuristic compares may similarly be grouped by the type of molecules that are affected by the changes. For example, molecules with a dedicated metabolic function may have a corresponding shading and/or pattern. This is shown in the example reaction network 502, where the metabolic change 512*b* is indicated with a specific molecule shading. Molecule B 503 may be involved in a cell's metabolic function. At its indicated location within the reaction network 502, it may have experienced an increase in concentration, or any other change from its baseline cell state. This is visually indicated to the user by the metabolic change 512*b* shading of molecule B 503. Similarly, molecule A 507 is shaded with the metabolic change 512*b* shading to indicate that molecule A 507 experiences a change from its baseline cell state associated with a metabolic change 512*b*.

Any other change other than a metabolic change 512*b* may be indicated by the shading of the reaction network 502. For example, changes associated with a sub-model of the whole cell model 200 may be color coded and indicated together within the reaction network 502. Additionally or alternatively, groupings of sub-models of the whole cell model 200 may be color coded and indicated together, such as all sub-models that simulate cell division, all sub-models that simulate DNA repair, etc.

B2. Time Lapse Correlation Heuristic

In some examples, the reaction network 502 may be displayed to a user simultaneously with a time lapse 508. In other examples, the time lapse 508 is displayed independently of the reaction network 502. The time lapse 508 displays changes associated with each of the molecule channels 514 across a time series of a simulation of the whole cell model 200. Each of the molecules and/or molecule categories in the molecule channels 514 may correspond to a molecule identifier within the reaction network 502. A change associated with any of the molecules and/or molecule categories within the molecule channels 514 is visually translated within the time lapse 508 to a change bar, such as change bar 516 in the protein molecule channel. The length of the change bars indicates the duration of the change across the time series. If a change occurs across more time steps, the change bar is extended, and if a change is no longer present, the change bar ends. A time lapse indicator 510 may allow a user to scroll within the time lapse 508, such that as the time lapse indicator 510 moves in the direction of the progression arrow 518. In response to a user moving the time lapse indicator 510 in the direction of the progression arrow 518, changes associated with time steps that occur later in the time lapse 508 are shown. Thus only a portion of the full time series of a simulation may be displayed within the time lapse 508 at a given time, but the full time lapse 508 is available to a user via scrolling the time lapse indicator 510.

In an example where the reaction network 502 and the time lapse 508 are displayed in a GUI together, the time lapse indicator 510 may be used to coordinate between the correlation visualization within the reaction network 502 and the visualization within the time lapse 508. The location of the time lapse indicator 510 within the time lapse 508 determines the changes that are simultaneously shown within the reaction network 502 by selecting a time step of a simulation within the time lapse 508. For example, the location of the time lapse indicator 510 as shown in illustration 500 corresponds to a time step in which the parameters for biomolecules, protein, RNA and DNA are all the same as a baseline cell state. This is indicated to a user by the lack of change bars that overlap the time lapse indicator 510 within these channels in the molecule channels 514. However, there is a metabolic change at the time shown by the time lapse indicator 510. This is shown in the time lapse 508 by the metabolic change 512c. The metabolic change 512c is also simultaneously shown within the reaction network 502 by the shading of different molecules, indicating that the metabolic change 512c is associated with the indicated molecules. When multiple changes within the molecule channels 514 occur at the time step selected by the time lapse indicator 510, each change may have a different shading within the reaction network 502. In response to movement of the time lapse indicator 510 (i.e., time progression through sequential time steps) the reaction network 502 shows the time lapse of changes associated with the change bars. Thus the reaction network 502 and the time lapse 508 are coordinated and dynamically adjust to display correlated changes in two different views to a user.

The correlation heuristic visualizations shown in illustration 500 visually align and display simultaneous changes to a user, providing simplified visual information to help a user understand the correlation between changes across different molecules or molecule groupings. The time lapse 508 situates correlated changes within a time progression to provide visual information about the relative occurrences of changes and their correlations over time. For example, the change bar 516 correlates to the metabolic change 512a, but not for the full duration of the metabolic change 512a. This is visually conveyed within the time lapse 508 by the partial overlap of the change bar 516 and the metabolic change 512a, allowing a user to understand the relative occurrence of the change bar 516 within the protein molecule channel and the metabolic change 512a within the metabolic channel. The reaction network 502 situates correlated changes within the physical location of the molecules affected by the change within the reaction network 200. This is visually conveyed within the reaction network 502 by the simultaneous shading of molecules in the reaction network 502, allowing a user to understand the physical relation of correlated changes within a reaction network.

C. Newness Heuristic

Figure 6:
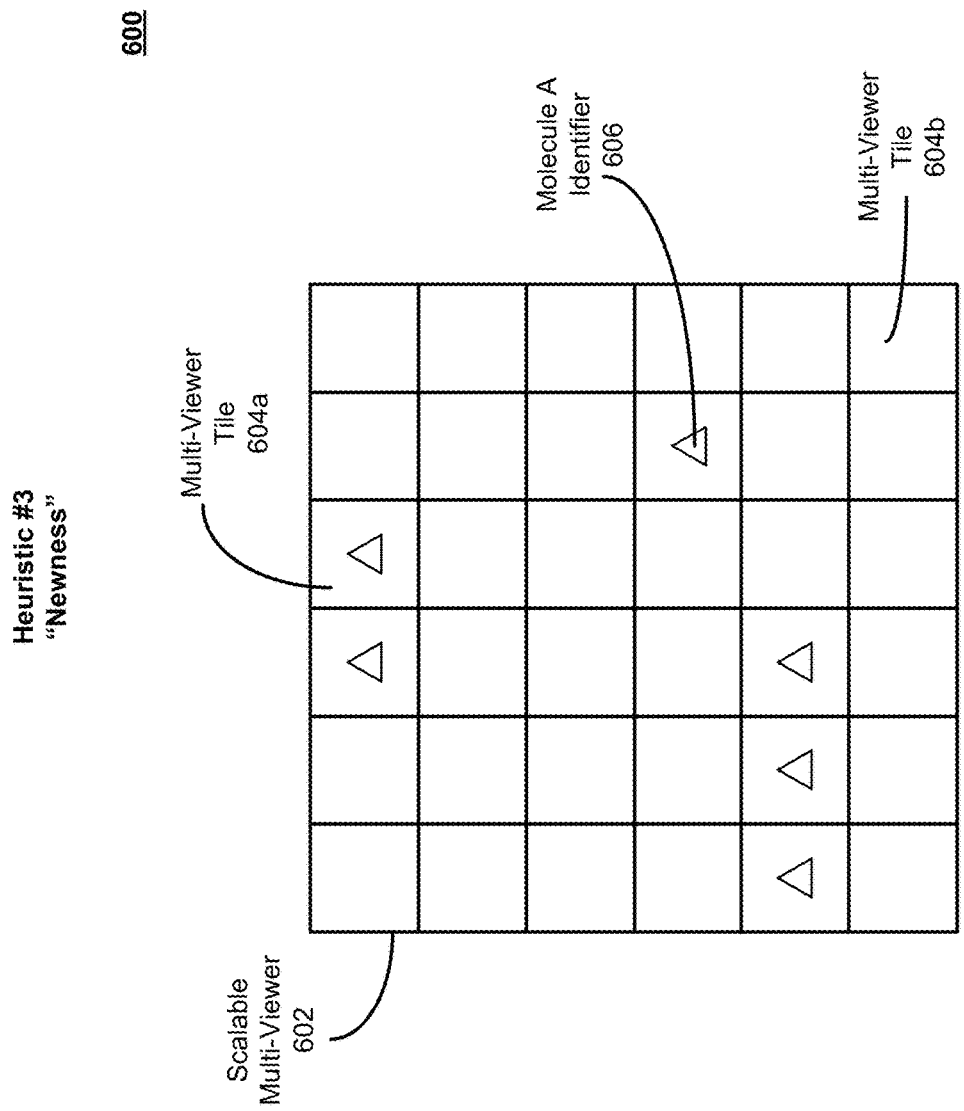
FIG. 6 is an illustration of a newness heuristic, according to one embodiment.

FIG. 6 is an illustration 600 of a newness heuristic, according to one embodiment. A newness heuristic evaluates how often a reaction with an associated change occurs within a reaction network 200. The newness heuristic compares the number of times a selected reaction occurs in a baseline cell state, and the number of times a selected reaction occurs in a perturbed cell state. In some examples, if the difference is above a threshold, the newness heuristic will visually convey this information to a user. For example, if a reaction is not present at all in a baseline cell state, and as a result of an input perturbation, the reaction occurs 20 times across various sub-models and locations within the whole cell model 200, the newness heuristic will convey this information to a user. In some examples, the newness heuristic may compare the number of times a reaction occurs in a previous time step to the number of times it occurs in a subsequent time step of a simulation. In some examples, the newness heuristic may compare the number of times a reaction has been verified to occur within in vivo results of a cell. For example, a user may want to know if, in response to an input perturbation, the whole cell model 200 has simulated a reaction that has never been confirmed in vivo, or if the reaction is commonly observed in vivo. The newness heuristic thus evaluates the uniqueness of a reaction with respect to a baseline cell, a previous simulation, a previous time step, and/or in vivo observations of cell behavior. The newness heuristic may be visually conveyed to a user within a scalable multi-viewer, as described below.

C1. Reaction Network Newness Heuristic

The newness heuristic is shown in FIG. 6 within a scalable multi-viewer 602, which may be the same scalable multi-viewer 402 as described in further detail with reference to FIG. 4A. The newness heuristic is visually conveyed to a user within the scalable multi-viewer by molecule identifiers, such as molecule A identifier 606, which are placed within multi-viewer tiles (e.g., multi-viewer tiles 604a and 604b) of the scalable multi-viewer 602. The presence of the molecule identifiers indicates that a molecule produced by a reaction is "new" and locates the reaction within its physical context in the whole cell model 200. Molecule identifiers, such as molecule A identifier 606, may be molecules that result from new reactions when the "newness" of the reaction is above a threshold value, such as a threshold number of occurrences between the simulation and the baseline cell state. In some examples, the molecule identifiers are displayed within the scalable multi-viewer 602 for a single time and a single simulation. In some examples, the molecule identifiers are displayed within the scalable multi-viewer 602 for a time interval and/or a number of simulations.

The newness heuristic as displayed in the scalable multi-viewer 602 allows a user to visually determine new reactions and their location within a reaction network. The scalable multi-viewer 602 visually deemphasizes portions of the scalable multi-viewer 602 that do not have new reactions, and allows a user to easily determine portions of a reaction network that may be important by indicating the newness of a molecule produced by the molecule identifiers.

D. Disruptive Heuristic

Figure 7:
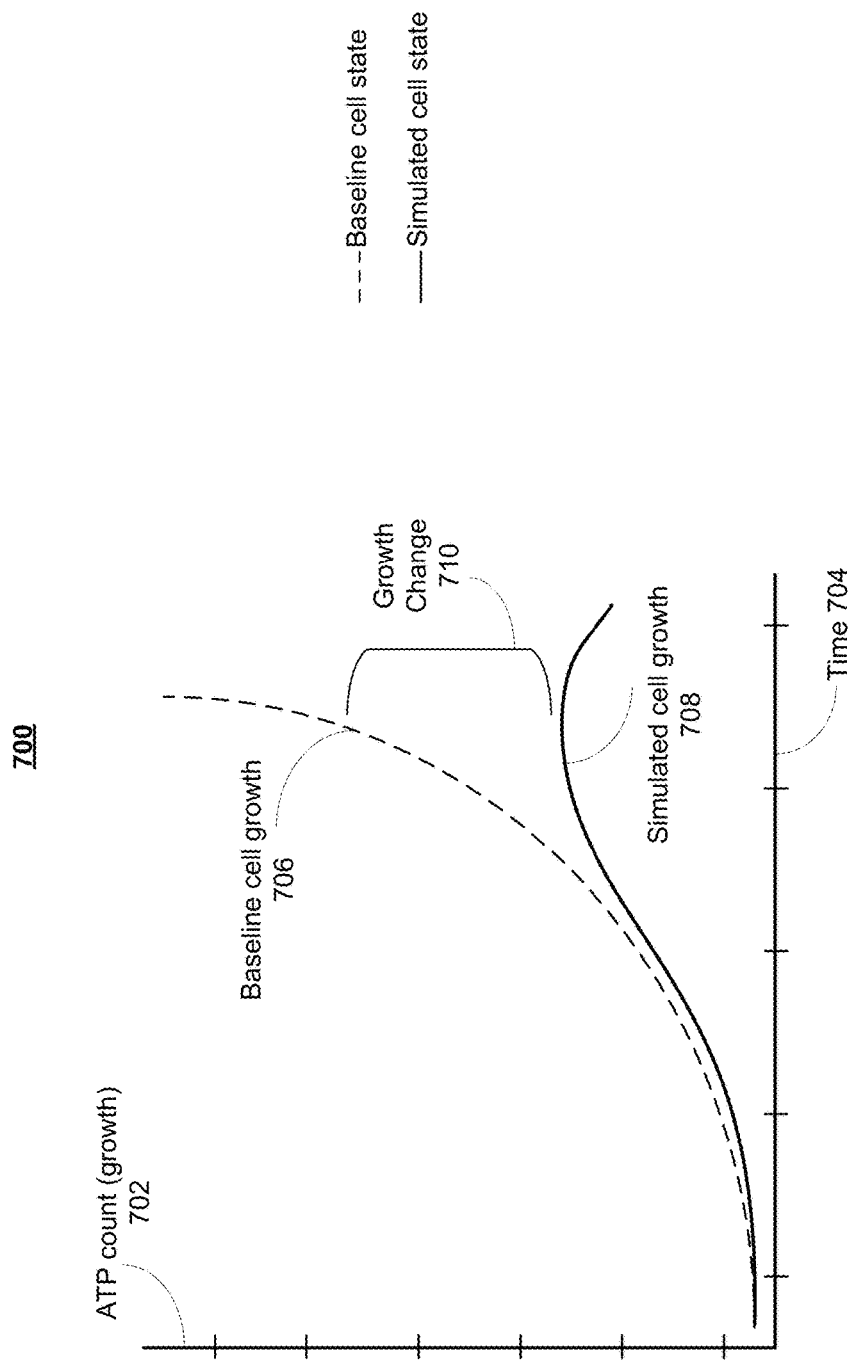
FIG. 7 is an illustration of a disruption heuristic, according to one embodiment.

FIG. 7 is an illustration 700 of a disruption heuristic, according to one embodiment. A disruptive heuristic evaluates the overall effect of an input perturbation on cell behavior over an extended time interval. The disruption heuristic aggregates changes in parameters across a number of different sub-models. For example, the disruption heuristic determines the long term survival or death of a cell by comparing final Adenosine triphosphate (ATP) concentrations to a baseline ATP concentration. In some examples, the disruption heuristic evaluates the long term survival or death of a cell by determining a final ATP concentration within a whole cell. In other examples, the disruption heuristic may determine the effect of an input perturbation on metabolism, gene expression, etc. by monitoring the concentration or molecule count of indicator molecules associated with these cell processes, such as overall DNA count, ATP production rates, etc. The disruption heuristic is conveyed to a user by a visualization, which is described in further detail below.

D1. Growth Disruptive Heuristic

The disruptive heuristic is conveyed to a user through a graph, shown in illustration 700, which compares the simulated cell growth 708 to a baseline cell growth 706. The graph shows the ATP count 702, and the time 704. The number of ATP molecules within a whole cell may thus be plotted over time within the graph. In some examples, the ATP count 702 may instead be an ATP concentration. The illustration 700 shows ATP molecule count, since the amount of ATP within a cell can be used as an indicator for cell growth. Illustration 700 shows both the baseline cell growth 706 and the ATP count that results from an input perturbation over the course of a time series simulation as the simulated cell growth 708. The visual comparison between the baseline cell growth 706 and the simulated cell growth 708 allows a user to distinguish the perturbation's effect on the whole cell growth, and more specifically the growth change 710 that results from an input perturbation.

The growth disruption heuristic visually conveys aggregate cell behavior within an entire cell or cell process, allowing a user to understand a global effect of an input perturbation.

E. Error Heuristic

Figure 8A:
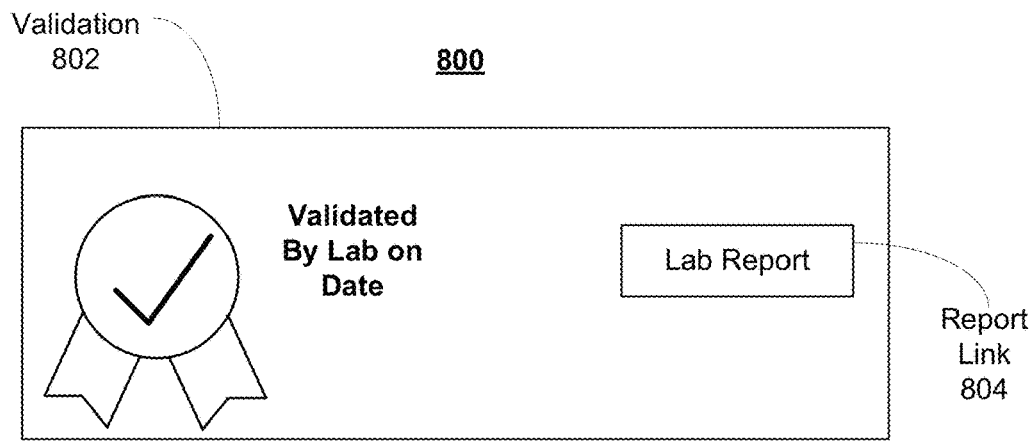
FIGS. 8A-8B are illustrations of an error heuristic, according to one embodiment.
Figure 8B:
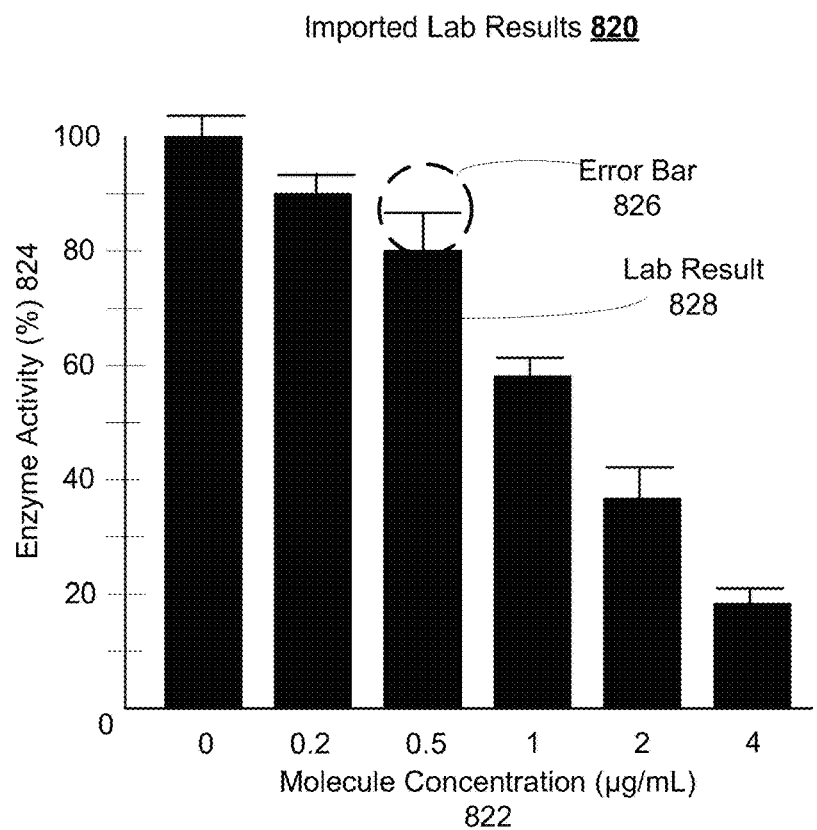

FIGS. 8A-8B are illustrations of an error heuristic, according to one embodiment. The error heuristic evaluates the output results of a simulation in comparison to in vivo or other groundtruth results to indicate the error associated with a simulation result. The error heuristic may evaluate the error of a simulation result associated with any of the parameters of a whole cell model, such as pH level, ATP concentration, cell death, changes in reaction rates, etc. The error heuristic may be determined by accessing a database of groundtruth cell behavior, primary source literature, or any other experimental results. The error heuristic is visually conveyed to a user as described in further detail below.

E1. Validation Error Heuristic

As shown in the illustration 800, the error heuristic of a simulation result may be visually conveyed to a user with a validation 802 indicator. The validation 802 simply indicates to a user that the result has been validated by an outside source, such as a journal or through in vivo testing. The illustration 800 provides a binary understanding of error to a user (i.e., validated or un-validated). To gain further details, a lab report may be accessed in response to a user input at the report link 804. The report link may then display the results of a validation experiment, a journal article, or any other source that was used to generate the validation 802.

E2. Lab Report Error Heuristic

The imported lab results 820 provide a more detailed understanding of the validation information used to determine an error heuristic for a simulation result. The imported lab results 820 are shown in FIG. 8B as an example, however any other standard biological lab results may be presented to a user. In FIG. 8B, molecule concentration 822 is shown versus a percent enzyme activity 824. The lab result 828 shows a particular enzyme activity for a specific molecule concentration, with the error bar 826 that indicates the uncertainty in the lab result. In some examples, this may be used to verify an enzyme reaction rate that results from a simulation in which the molecule concentration is perturbed. The error heuristic would then use the imported lab results 820 to verify the reaction rate given the input perturbation of the molecule concentration, and convey this to a user.

The error heuristic allows a user to contextualize and verify the simulation results produced by the whole cell model 200 versus outside laboratory results. This may help a user understand if the simulation results are commonly seen in a lab, or if the results are an anomaly and should be investigated further.

F. Span Heuristic

Figure 9:
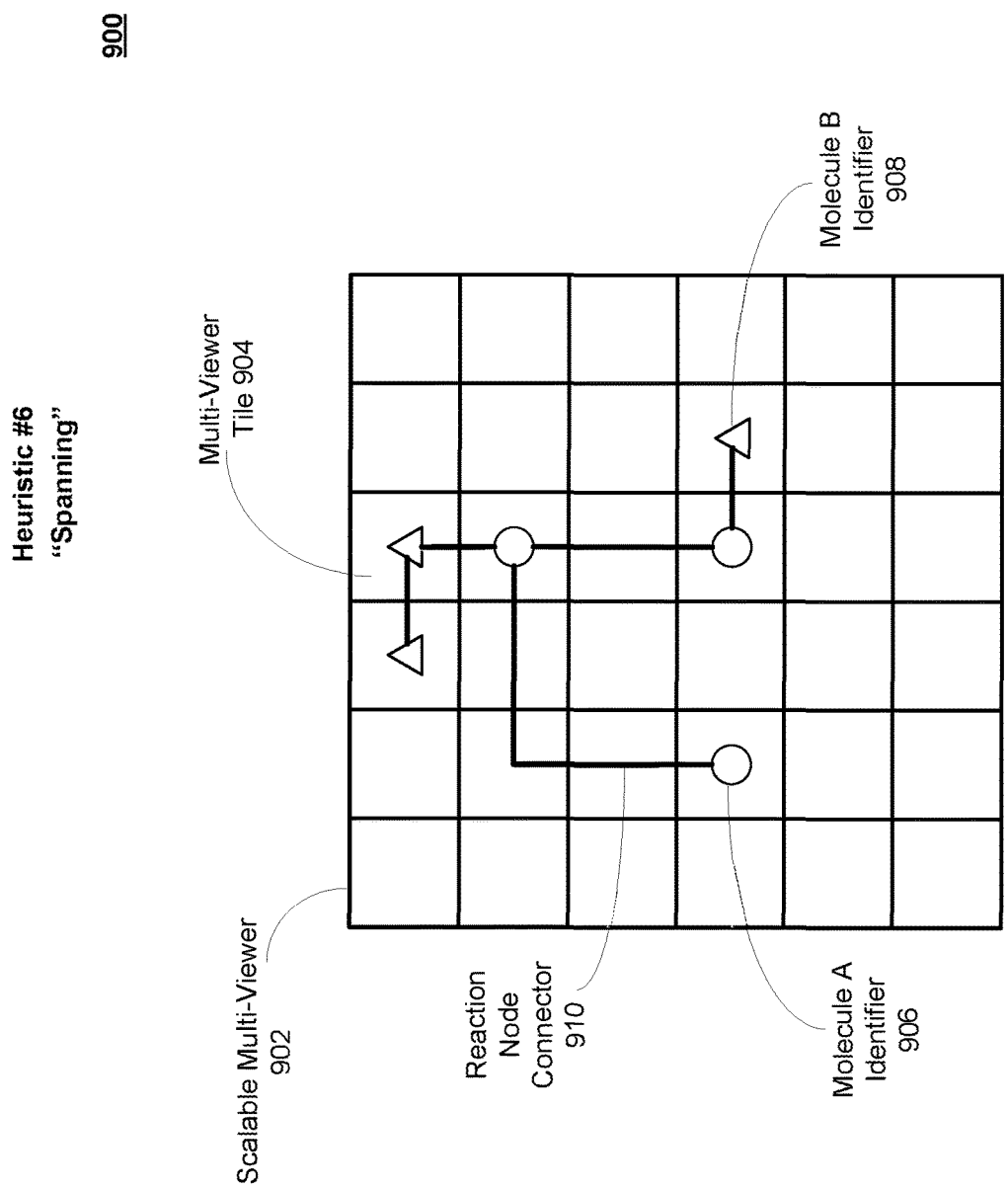
FIG. 9 is an illustration of a span heuristic, according to one embodiment.

FIG. 9 is an illustration 900 of a span heuristic, according to one embodiment. The span heuristic evaluates how many different sub-processes, reaction nodes and/or molecule nodes are affected by an input perturbation. The span heuristic thus traces linked changes across the whole cell model 200. The span heuristic may be evaluated by tracing linked molecule nodes and process nodes within a reaction network. For example, if a first molecule has an increase in concentration as a result of an input perturbation, the span heuristic may determine all of the linked molecule and process nodes to the first molecule. In some examples, the span heuristic may determine linked molecule and process nodes that themselves have a change above a threshold. The span heuristic is visually conveyed to a user by displaying the linked set of molecule and process nodes, and their physical relation to each other within a reaction network. The visualization of the span heuristic is described in more detail below.

F1. Scalable Multi-viewer Span Heuristic

The span heuristic may be displayed to a user within a scalable multi-viewer 902, which may be the scalable multi-viewer 402 as described in further detail with reference to FIG. 4A. The span heuristic is displayed within the scalable multi-viewer 902 by indicating the linked molecule and process nodes affected by an input perturbation, and their physical relation within the scalable multi-viewer 902. In some examples, each of the molecules may have a unique molecule identifier, such as the molecule B identifier 908. Molecule B may have an increased concentration as a result of an input perturbation. This may then produce increased concentrations of linked molecule nodes and increased reaction rates for linked process nodes, such as the connected molecule indicated by the molecule A identifier 906 and the reaction node connector 910. Each of the molecules and reaction node connectors are overlaid on the multi-viewer tiles, such as the multi-viewer tile 904. Each multi-viewer tile may represent a single molecule node and/or a single process node. In other examples, each multi-viewer tile may represent a cluster or linked set of molecule and/or process nodes within a reaction network.

The span heuristic thus visually conveys to a user the distributive effect of a perturbation across linked molecule nodes and process nodes of a reaction network. The span heuristic allows a user to visually understand the linked connection between changes across the reaction network.

G. Inter-dependence Heuristic

Figure 10:
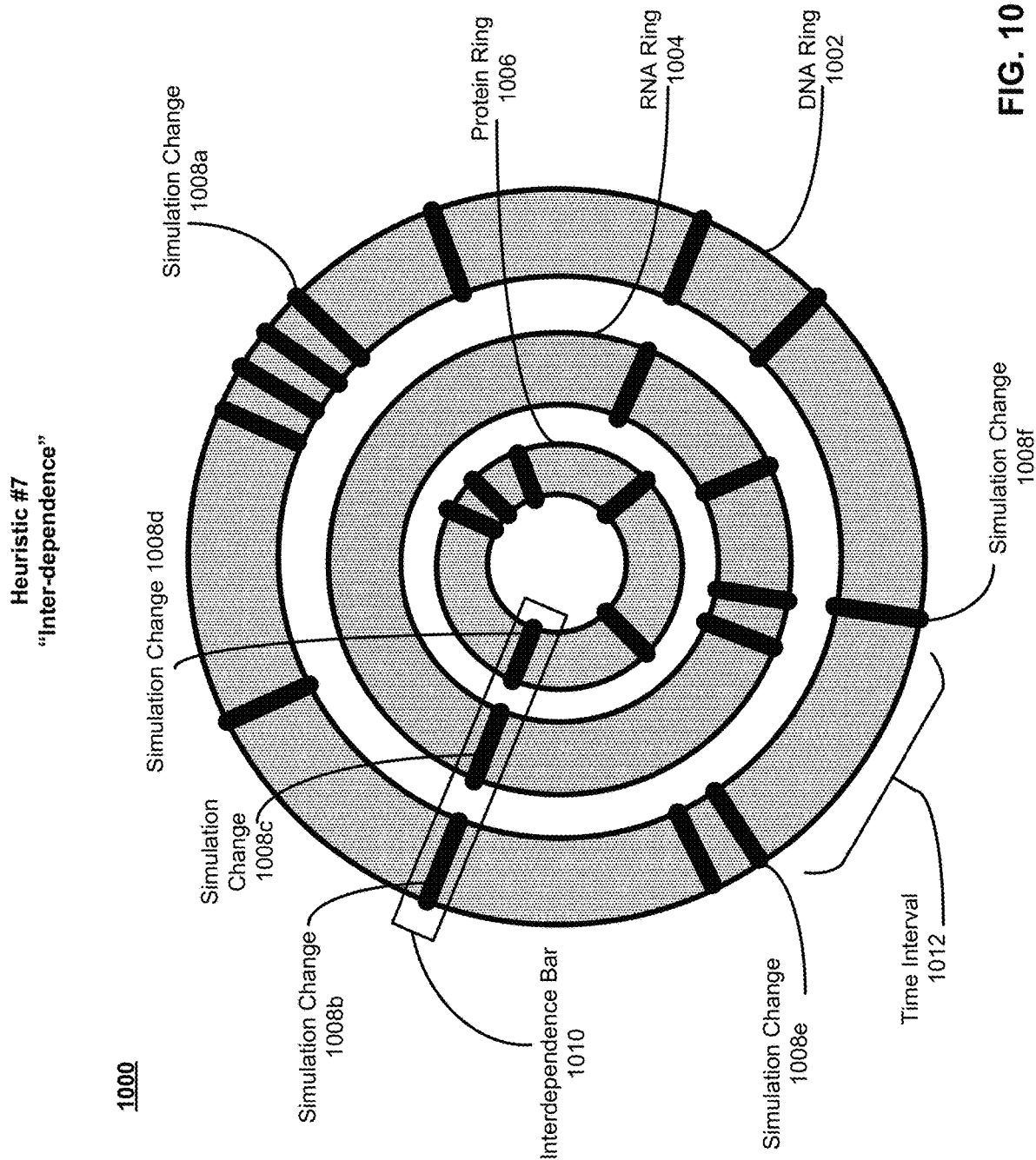
FIG. 10 is an illustration of an inter-dependence heuristic, according to one embodiment.

FIG. 10 is an illustration 1000 of an inter-dependence heuristic, according to one embodiment. An interdependence heuristic evaluates the correlation between changes across different molecules, sub-processes, molecule categories, or any other groupings within the reaction network. The interdependence heuristic may be determined using any standard statistical calculation of codependence between variables. The interdependence heuristic may be distinct from the span or the correlation heuristics in that it may determine interdependence of changes between non-linked process and between changes that are not necessarily coincident in time. The interdependence heuristic may compare changes across different molecule nodes, process nodes, and/or sub-models within a single simulation and time in a time series. Additionally or alternatively, the interdependence heuristic may compare changes across a time interval. The interdependence heuristic is visually conveyed to a user as described below.

G1. Nested Rings Inter-Dependence Heuristic

The interdependence heuristic is visually conveyed to a user in the nested rings 1000. Each ring represents a different set of molecules, processes and/or sub-model groupings. As shown in FIG. 10, the DNA ring 1002 represents molecule nodes, process nodes and sub-models associated with DNA, RNA ring 1004 represents molecule nodes, process nodes and sub-models associated with RNA, and the protein ring 1006 represents molecule nodes, process nodes and sub-models associated with proteins. The nested rings 1000 align change markings on the rings to indicate that the changes are interdependent. Change markers, such as the simulation change 1008a, indicate instances where an input perturbation has altered any of the parameter values from those of a baseline cell within the ring grouping. For example, the simulation change 1008e on the DNA ring 1002 indicates that a change in any of the parameters associated with DNA have been altered by an input perturbation from a baseline cell state. The spacing between changes is proportional to a time interval between the changes in a time series of a simulation. For example, the time interval 1012 between simulation change 1008e and a simulation change 1008f is proportional to the time difference between the time the simulation change 1008e occurred and the time the simulation 1008f occurred.

As shown in FIG. 10, at the interdependence bar 1010, the simulation change 1008b, simulation change 1008c and simulation change 1008d are aligned together, indicating that these change bars are interdependent. The nested rings 1000 thus convey interdependent changes within different groupings to a user, allowing a user to visually determine which simulation changes may be related to each other.

VIII. Heuristic Ranking Example

Figure 11:
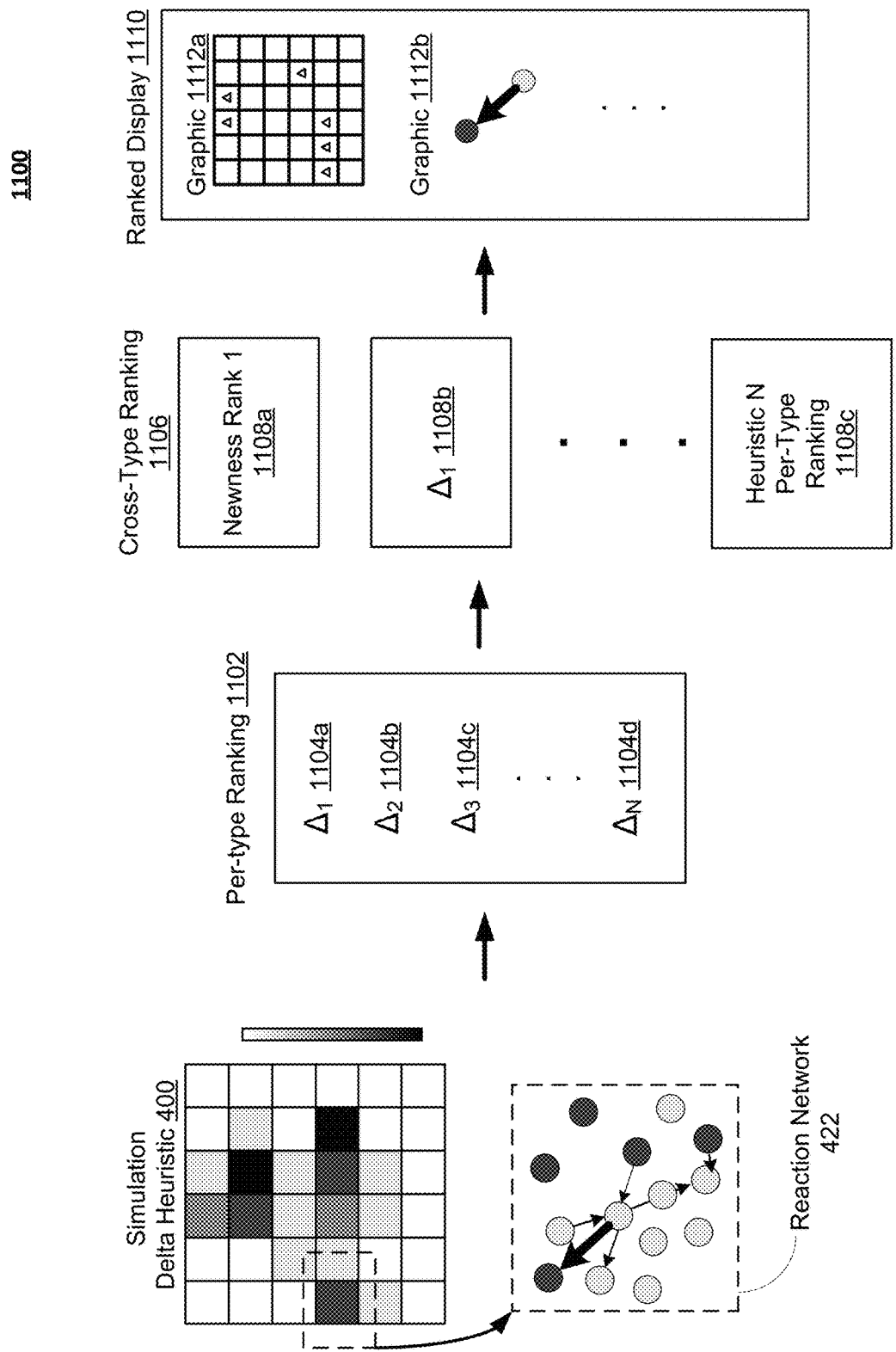
FIG. 11 is an illustration of the process for ranking a set of outcomes of a simulation of a biological cell starting with an example delta heuristic, according to one embodiment.

FIG. 11 is an illustration 1100 of the process for ranking a set of outcomes of a simulation of a biological cell starting with an example delta heuristic, according to one embodiment. The process of illustration 1100 is the process 300 as discussed in further detail with reference to FIG. 3. The delta heuristic is the delta heuristic as described in further detail with reference to FIGS. 4A-4B. The process first accesses 302 a set of outcomes of the simulation of a biological cell. This may be accessing the simulation data for at least one simulation. The process then determines, from the simulation data, a simulation delta heuristic, which may be displayed as shown in illustration 400 or as a reaction network 422. Following determining the delta heuristic from the simulation data, the process 300 then determines the per-type ranking 1102. The per-type ranking 1102 is determined by ranking within the delta heuristic and a single time step, the delta heuristic data. For example, there may be a delta heuristic for any number of molecule nodes, process nodes, and simulation parameters, and of which may be evaluated with a simulation heuristic. This results in the per-type ranking 1102, where, for example, a $\Delta_1$ 1104a may be greater in magnitude than the $\Delta_2$ 1104b, $\Delta_3$ 1104c and $\Delta_N$ 1104d. In this example, the per-type ranking 1102 may rank each delta heuristic by its magnitude, producing a ranked list of the most to least change in each parameter.

The per-type ranking 1102 is then used to generate a cross-type ranking 1106. The process ranks 306, across at least two heuristics and two time steps, each of the set of outcomes to form a cross-type rankings 1106. The comparison between heuristics measures a distance-to-intent between the heuristics within the per-type ranking 1102 and the input perturbation. Process 300 thus determines a correlation between the input perturbation and each of the heuristics within the per-type ranking 1102. As shown in the cross-type ranking 1106, different heuristics may have a stronger correlation to the input perturbation. For example, the newness rank 1 1108a may have a stronger correlation to the input perturbation than the delta heuristic $\Delta_1$ 1108b and is thus ranked higher. The cross-type ranking 1106 may rank all heuristics within the per-type rankings 1108c. In other examples, the cross-type ranking 1106 ranks a portion of the per-type rankings.

Figure 12:
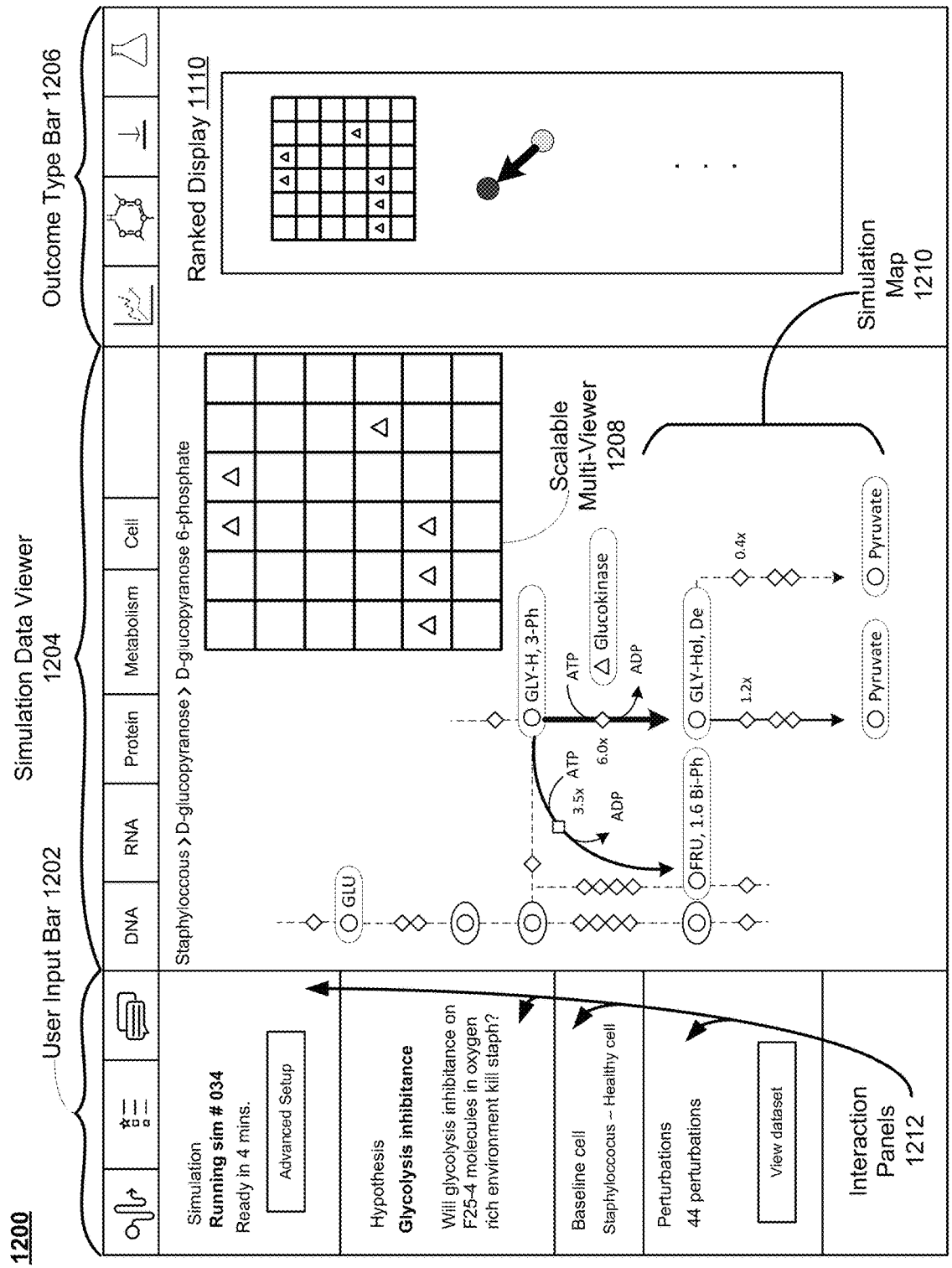
FIG. 12 is an illustration of a graphical user interface (GUI) of the simulation system with ranked heuristics of FIG. 11, according to one embodiment.

Process 300 then provides a ranked display 1110 by converting between the cross-type ranking 1106 and the visualizations associated with each of the heuristics. Thus each of the heuristics in the cross-type ranking 1106 are displayed using the visualization unique to each heuristic. For example, the newness rank 1 1108a is shown as graphic 1112a within the ranked display 1110. The $\Delta_1$ 1104a is shown as graphic 1112b within the ranked display 1110. Each of the heuristics within the cross-type ranking 1106 may be displayed within the ranked display 1110 by their unique visualizations, as described in further detail with reference to FIGS. 4A-10. The ranked display 1110 is then displayed to a user, allowing a user to easily determine more and less important simulation data with respect to the user's input perturbation. The ranked display 1110 may be displayed within a GUI. An example GUI is described in further detail below. FIG. 12 is an illustration of a GUI 1200 of the simulation system with ranked heuristics of FIG. 11, according to one embodiment. The simulation system runs one or more simulations generating a separate set of simulation data per simulation. The GUI 1200 may be displayed through a display device of a computing device, specifically through a web page, an application, or another software or firmware mechanism. The GUI 1200 presents a number of graphical elements within the GUI in different portions of a display area of the display device. Each such graphical element presents various pieces of information about simulations of a whole cell model, the reaction network 200, and simulation data from one or more of the simulations. In one embodiment, the graphical elements of the GUI 1200 include a user input bar 1202, a simulation data viewer 1204, and an outcome type bar 1206, each of which is a window in the GUI 1200.

A. User Input Bar

In this example embodiment, the user input bar 1202 comprises a plurality of interaction panels 1212. In one embodiment, one of the interaction panels 1212 includes a page button for toggling simulation parameters, another page button for accessing previous run experiments and/or specific simulations, and another page button for accessing threads of comments between collaborators on particular experiments and/or simulations.

The GUI 1200 may receive a user input selecting the page for toggling simulation parameters. In response, the user input bar 1202 displays a page title corresponding to the page for toggling simulation parameters. The interaction panels 1212 associated with simulation parameters may each display one or more parameters for perturbing a cell. In one interaction panel, one or more buttons may prompt a user to provide input for a simulation. In another interaction panel 1212, a button starts a simulation. The user input bar 1202 thus receives an input perturbation from a user, and uses this perturbation information to generate a simulation of a whole cell.

In some embodiments, a user may input a hypothesis into the user input bar 1202, such as a question or statement that a user is attempting to answer through simulation of a whole cell model. In some embodiments, the user input bar 1202 uses natural language processing (NLP) to convert the input hypothesis into a mathematical perturbation of a baseline cell. For example, if a user inputs a hypothesis about the importance of a specific enzyme, the user input bar 1202 may convert this question to a decrease in the concentration of that enzyme, allowing the user to view simulation data that restricts the enzyme quantity. The user may then be able to better understand the role of the enzyme within a reaction network, sub-model, or any other element of the whole cell model of interest to the user.

B. Simulation Data Viewer

The simulation data viewer 1204 displays simulation data in response to a user input in the user input bar 1202. The simulation data viewer 1204 may display any number of visualizations, such as a reaction network, the whole cell model 200, or any of the heuristics described in FIGS. 4A-10. As shown in FIG. 12, the simulation data viewer displays a scalable multi-viewer 1208 and a simulation map 1210 which displays a portion of a reaction network. The simulation data viewer may display per-type rankings, such as the per-type ranking 1102 as described in further detail with reference to FIG. 11.

C. Outcome Type Bar

The outcome type bar 1206 displays outcomes of the simulation initiated within the user input bar 1202 by a user input. The outcome type bar 1206 displays the ranked display 1110 that results from a cross-type ranking. The ranked display 1110 allows a user to visually identify important outcomes within the simulation data, which may otherwise be difficult to discern from the simulation data displayed within the simulation data viewer 1204.

In some embodiments, in addition to generating the ranked display 1110 through a correlation calculation between the heuristics and an input perturbation, the ranked display 1110 may be adjusted in response to a user interaction with the GUI. For example, the outcome type bar 1206 may weight heuristics within the ranked display 1110 based on the number of times a user has requested to view the heuristic when it is displayed in the ranked display 1110. The GUI may log any user interaction with the ranked display 1110, such as the time a user spends viewing a heuristic in the ranked display 1110, and use the user interaction as feedback to tailor the ranked display 1110 to a particular user's interests.

IX. Additional Considerations

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A method for ranking a set of outcomes of a simulation of a biological cell, the method comprising:

accessing a set of outcomes of the simulation of the biological cell, wherein each outcome is associated with a time step of the simulation and an outcome type of a plurality of outcome types, wherein the simulation of the biological cell includes applying a perturbation to the simulation of the biological cell, wherein the perturbation includes modifying one or more input variables of the simulation to effect an addition or blocking of a reaction pathway associated with the biological cell, and wherein each outcome type of the plurality of outcome types is configured to be displayed as a particular graphic representation on a first portion of a graphical user interface;

ranking, within the outcome type and the time step, each outcome of the set of outcomes to form a set of per-type outcome rankings for that time step;

ranking, across at least two outcome types and at least two time steps, the set of outcomes to form a cross-type outcome ranking; and providing for display to a user a ranked list from the set of per-type outcome rankings and the cross-type outcome ranking, wherein the ranked list is determined based at least in part on a correlation between each outcome and the perturbation of the simulation of the biological cell, and wherein the ranked list includes a ranking of the plurality of outcome types that are configured to be displayed by their respective graphic representations on a second portion of the graphical user interface.

2. The method of claim 1, wherein each outcome is associated with a simulation number, a subunit of the biological cell, and the perturbation of the simulation of the biological cell.

3. The method of claim 2, wherein the ranking, across at least two outcome types and two time steps, each of the set of outcomes to form the cross-type outcome ranking further comprises:

ranking across at least two subunits.

4. The method of claim 2, wherein the ranking, across at least two outcome types and two time steps, each of the set of outcomes to form the cross-type outcome ranking further comprises:

ranking across at least two simulations.

5. The method of claim 2, wherein the ranking, across at least two outcome types and two time steps, each of the set of outcomes to form the cross-type outcome ranking further comprises:

ranking across at least two perturbations.

6. The method of claim 1, wherein the simulation of the biological cell is a mathematical calculation across at least two time steps of a behavior of a connected network of a plurality of molecule nodes and a plurality of process nodes, wherein each molecule node comprises a molecule in the biological cell and each process node comprises a biochemical process in the biological cell.

7. The method of claim 1, wherein the plurality of outcome types includes at least one of: a delta, a correlation, a newness, a disruptive factor, an error, a span, and an inter-dependence.

8. The method of claim 1, wherein the perturbation further includes at least one of: removing a molecule from the simulation, removing a nucleic acid from the simulation, removing a growth factor from the simulation, adding a molecule to the simulation, adding a nucleic acid to the simulation, adding a growth factor to the simulation.

9. The method of claim 1, further comprising:

tracking an interaction of the user with the ranked list from the set of per-type outcome rankings and the cross-type outcome ranking.

10. A non-transitory computer-readable storage medium storing instructions for ranking a set of outcomes of a simulation of a biological cell, the instructions when executed causing a processor to perform operations comprising:

accessing a set of outcomes of the simulation of the biological cell, wherein each outcome is associated with a time step of the simulation and an outcome type of a plurality of outcome types, wherein the simulation of the biological cell includes applying a perturbation to the simulation of the biological cell, wherein the perturbation includes modifying one or more input variables of the simulation to effect an addition or blocking of a reaction pathway associated with the biological cell, and wherein each outcome type of the plurality of outcome types is configured to be displayed as a particular graphic representation on a first portion of a graphical user interface;

ranking, within the outcome type and the time step, each outcome of the set of outcomes to form a set of per-type outcome rankings for that time step;

ranking, across at least two outcome types and at least two time steps, the set of outcomes to form a cross-type outcome ranking; and providing for display to a user a ranked list from the set of per-type outcome rankings and the cross-type outcome ranking, wherein the ranked list is determined based at least in part on a correlation between each outcome and the perturbation of the simulation of the biological cell, and wherein the ranked list includes a ranking of the plurality of outcome types that are configured to be displayed by their respective graphic representations on a second portion of the graphical user interface.

11. The computer-readable storage medium of claim 10, wherein each outcome is associated with a simulation number, a subunit of the biological cell, and the perturbation of the simulation of the biological cell.

12. The computer-readable storage medium of claim 11, wherein the ranking, across at least two outcome types and two time steps, each of the set of outcomes to form the cross-type outcome ranking further comprises:

ranking across at least two subunits.

13. The computer-readable storage medium of claim 11, wherein the ranking, across at least two outcome types and two time steps, each of the set of outcomes to form the cross-type outcome ranking further comprises:

ranking across at least two simulations.

14. The computer-readable storage medium of claim 11, wherein the ranking, across at least two outcome types and two time steps, each of the set of outcomes to form the cross-type outcome ranking further comprises:

ranking across at least two perturbations.

15. The computer-readable storage medium of claim 10, wherein the simulation of the biological cell is a mathematical calculation across at least two time steps of a behavior of a connected network of a plurality of molecule nodes and a plurality of process nodes, wherein each molecule node comprises a molecule in the biological cell and each process node comprises a biochemical process in the biological cell.

16. The computer-readable storage medium of claim 10, wherein the plurality of outcome types includes at least one of: a delta, a correlation, a newness, a disruptive factor, an error, a span, and an inter-dependence.

17. The computer-readable storage medium of claim 10, wherein the perturbation further includes at least one of: removing a molecule from the simulation, removing a nucleic acid from the simulation, removing a growth factor from the simulation, adding a molecule to the simulation, adding a nucleic acid to the simulation, adding a growth factor to the simulation.

18. The computer-readable storage medium of claim 10, further comprising:

tracking an interaction of the user with the ranked list from the set of per-type outcome rankings and the cross-type outcome ranking.

* * * * *